United States Patent
Kasher et al.

(10) Patent No.: US 9,175,036 B2
(45) Date of Patent: Nov. 3, 2015

(54) ANTIMICROBIAL WATER TREATMENT MEMBRANES AND PRODUCTION THEREOF

(75) Inventors: Roni Kasher, Midreshet Ben-Gurion (IL); Ze'ev Ronen, Midreshet Ben-Gurlon (IL); Ehud Banin, Tel-Aviv (IL)

(73) Assignees: BEN-GURION UNVERSITY OF THE NEGEV RESEARCH AND DEVELOPMENT AUTHORITY, Beer-Sheva (IL); BAR-ILAN UNIVERSITY, Ramat-Gan (IL)

( * ) Notice: Subject to any disclaimer, the term of this patent is extended or adjusted under 35 U.S.C. 154(b) by 599 days.

(21) Appl. No.: 13/514,103

(22) PCT Filed: Dec. 7, 2010

(86) PCT No.: PCT/IL2010/001034
§ 371 (c)(1),
(2), (4) Date: Aug. 15, 2012

(87) PCT Pub. No.: WO2011/070573
PCT Pub. Date: Jun. 16, 2011

(65) Prior Publication Data
US 2012/0325748 A1    Dec. 27, 2012

Related U.S. Application Data

(60) Provisional application No. 61/267,099, filed on Dec. 7, 2009.

(51) Int. Cl.
*B01D 61/00*    (2006.01)
*B01D 39/00*    (2006.01)
(Continued)

(52) U.S. Cl.
CPC .............. *C07K 5/1019* (2013.01); *B01D 65/08* (2013.01); *B01D 67/0093* (2013.01); *B01D 69/144* (2013.01); *C07K 17/06* (2013.01); *C07K 17/08* (2013.01); *B01D 61/025* (2013.01);
(Continued)

(58) Field of Classification Search
CPC ......... C02F 1/44; C07D 207/40; A61K 38/00
USPC .......... 210/652, 651, 500.38, 500.28; 264/48; 548/546; 427/180; 436/86; 424/423
See application file for complete search history.

(56) References Cited

U.S. PATENT DOCUMENTS 6,197,529 B1 *   3/2001   Houghten et al. .............. 506/15
7,172,276 B2 *   2/2007   Breton et al. ................. 347/100
(Continued)

FOREIGN PATENT DOCUMENTS

JP    2009 165949    7/2009

OTHER PUBLICATIONS

European Extended Search Report dated Jul. 8, 2014 in European Application No. 10 835 606.4.
(Continued)

*Primary Examiner* — Ana Fortuna
(74) *Attorney, Agent, or Firm* — Nixon & Vanderhye P.C.

(57) ABSTRACT

The present invention discloses antimicrobial water treatment membranes, comprising a water treatment membrane, covalently attached to one or more antimicrobial peptides or derivatives thereof, either directly or via one or more tether molecules. There are also provided a process for preparing these antimicrobial membranes, and uses thereof in water treatment applications.

17 Claims, 7 Drawing Sheets

(51) Int. Cl.
*B01D 39/14* (2006.01)
*B01D 67/00* (2006.01)
*C07K 5/11* (2006.01)
*B01D 65/08* (2006.01)
*B01D 69/14* (2006.01)
*C07K 17/06* (2006.01)
*C07K 17/08* (2006.01)
*B01D 61/02* (2006.01)
*B01D 61/14* (2006.01)

(52) U.S. Cl.
CPC ............ *B01D61/027* (2013.01); *B01D 61/145* (2013.01); *B01D 2321/168* (2013.01); *B01D 2323/38* (2013.01); *B01D 2325/48* (2013.01)

(56) References Cited

U.S. PATENT DOCUMENTS

| | | | |
|---|---|---|---|
| 2003/0050247 A1* | 3/2003 | Kuhner et al. | 514/16 |
| 2007/0254006 A1* | 11/2007 | Loose et al. | 424/423 |
| 2009/0022888 A1* | 1/2009 | Neff et al. | 427/180 |
| 2011/0288011 A1* | 11/2011 | Castaigne et al. | 514/5.3 |
| 2012/0325748 A1* | 12/2012 | Kasher et al. | 210/652 |
| 2014/0238939 A1* | 8/2014 | Kasher et al. | 210/650 |

OTHER PUBLICATIONS

K. Berliner et al., "Immobilization of Antimicrobial Peptides on Reverse Osmosis Polyamide Membranes: Potential Biofilm Inhibitors?", Advances in Experimental Medicine and Biology, Springer, US, vol. 611, Jan. 1, 2009, pp. 241-242, XP008156836.

K. Berliner et al; "Immobilization of Antimicrobial Peptides on Reverse Osmosis Polyamide Membranes: Potential Biofilm inhibitors?", Biopolymers, John Wiley & Sons, Inc, US, vol. 88, No. 4, Sp. Issue, Jan. 1, 2007, p. 602, XP008169916.

R. Bessalle et al; "Structure-Function Studies of Amphiphilic Antibacterial Peptides", Journal of Medicinal Chemistry, American Chemical Society, US, vol. 36, No. 9, Jan. 1, 1993, pp. 1203-1209, XP002024716.

* cited by examiner

ANTIMICROBIAL WATER TREATMENT MEMBRANES AND PRODUCTION THEREOF

This application is the U.S. national phase of International Application No. PCT/IL2010/001034 filed Dec. 7, 2010 which designated the U.S. and claims priority to U.S. Provisional Application No. 61/267,099 filed Dec. 7, 2009, the entire contents of each of which are hereby incorporated by reference.

Membranes, such as thin film composite (TFC) membranes for reverse osmosis (RO), nanofiltration (NF) and ultrafiltration (UF) are currently the most common membranes used in technologies for drinking water production and are widely used in water treatment processes such as desalination, ultra-pure water production and industrial or municipal waste-water treatment.

A major problem in the field of water production is the formation of biofilm. Biofilm is an aggregate of microorganisms in which cells adhere to each other and/or to a surface. These cells are frequently embedded in a self-produced matrix of extra-cellular polymeric substance (also referred to as slime). Biofilm may form on living or non-living surfaces, such as on membranes used in water treatment processes, where there is a continuous supply of nutrients, a supply which promotes microorganism reproduction and accelerates bacterial growth.

Current methods for prevention and treatment of biofilm include pretreatment of the feed in RO applications, to limit biofouling. This method is costly as it requires additional equipment, and is not very efficient due to the continuous supply of nutrients in the feed which, as mentioned above, promotes and accelerates biofilm formation on the membrane surface. A second method is periodical cleaning of the RO membrane module, as for example by using detergents and alterations of acidic (usually citric acid) and basic solutions. However, this practice requires suspending of desalination process, which reduces its capacity. Furthermore, biofilm removal by cleaning is not effective enough, and there is no backwash in RO, and hence biofilm gradually accumulates.

Another strategy involves modification of the membrane surface to render it less susceptible to biofouling. For example, the hydrophilic character of the membrane surfacer can be increased by graft polymerization using hydrophilic monomers onto RO and NF membranes (e.g., Belfer et al. *Journal of Membrane Science* 55-64, 239, 2004). These methods, while improving membrane resistance to organic fouling, have not been successful in preventing biofouling.

Effective prevention of microbial growth on membranes is currently achieved only when a continuous, high chlorine concentration is maintained. However, chlorine generates harmful by-products upon reaction with organic matter, making this method unsuitable for most water treatment applications. Additionally, the most commonly used water treatment membranes are sensitive to oxidizing agents such as chlorine and ozone.

The use of antimicrobial peptides has been suggested in industrial processes which include the use of RO membranes (US 20020051819, US 20030050247, US 20030194445, US 20050065072 and US 20060166883).

Antimicrobial peptides (AMPs) are small molecular weight proteins with broad spectrum antimicrobial activity against bacteria, viruses, and fungi. These evolutionarily conserved peptides are produced in all types of living organisms and serve as part of each organism's innate immunity. AMPs are usually positively charged, enabling them to strongly bind to the negatively charged outer cell membrane of prokaryotes, thereby enhancing antimicrobial activity.

Methods for attaching AMPs to surfaces with the aim of bestowing these surfaces with anti microbial properties, have been described (e.g., Gabriel et al., Bi-conjugate Chem. 548-550, 17(2), 2006 and Glinel et al. Bio-conjugate Chem. 71-77, 20(1), 2009). However, these methods include the use of organic solvents and are thus inappropriate for use in applications using TFC membranes due to the sensitivity of TFC membranes to organic solvents.

Furthermore, although the use of AMPs in reverse osmosis has been suggested in several publications (Berliner, K. et al, Biopolymers 2007, Vol. 88 (4), 602-602 and Berliner, K. et al, Peptides for Youth—The Proceedings of the 20th American Peptide Symposium, in Advances in Experimental Medicine and Biology 2009 (Editors): DelValle S; Escher E; Lubell W D), Volume 611, 241-242) these publications do not provide any practical teaching in this matter: there is no teaching of which AMPs would be appropriate for this task nor is there any teaching of how AMPs would be attached to water treatment membranes while preserving their antimicrobial activity.

Thus, to date, there has been no report on the use of surface-attached AMPs as antibacterial agents for the prevention of biofilm growth and biofouling of Water treatment membranes in processes of water treatment.

Presently, prevention and treatment of biofilm formation on water treatment membranes is a major obstacle in water treatment processes, acting as a barrier to large scale utilization of these membranes. A safe and efficient solution for the problem of biofouling of Water treatment membranes is greatly needed.

The present inventors have now developed novel antibacterial water treatment membranes, which comprise Water treatment membranes, linked to suitable antimicrobial peptides or their suitable derivatives, optionally and preferably via pre-defined spacers (tethers) and linkers.

As shown in the experimental section which follows, these modified membranes have proven antibacterial activity as well as stability, and can be used in both saline and non-saline environments, thus rendering them most suitable for a wide variety of water purification applications which are susceptible to biofouling and biofilm formation.

Thus, according to one aspect of the invention, there is provided an antimicrobial water treatment membrane comprising a water treatment membrane, covalently attached to one or more antimicrobial peptides or derivatives thereof, either directly or via tethers (spacers) and/or linkers.

Water treatment membranes are classified according to their permeability and uses, as detailed above. The present invention is suitable to Reverse Osmosis (RO) membranes, Nano Filtration (NF) membranes, and also to Ultra Filtration (UF) and Micro Filtration (MF) membranes, as long as these membranes can covalently link, or can be modified to link, to an antimicrobial peptide (AMP) either directly or via a tether molecule.

Preferably, the water treatment membrane of the present invention is an RO or NF membrane.

Figure 1:
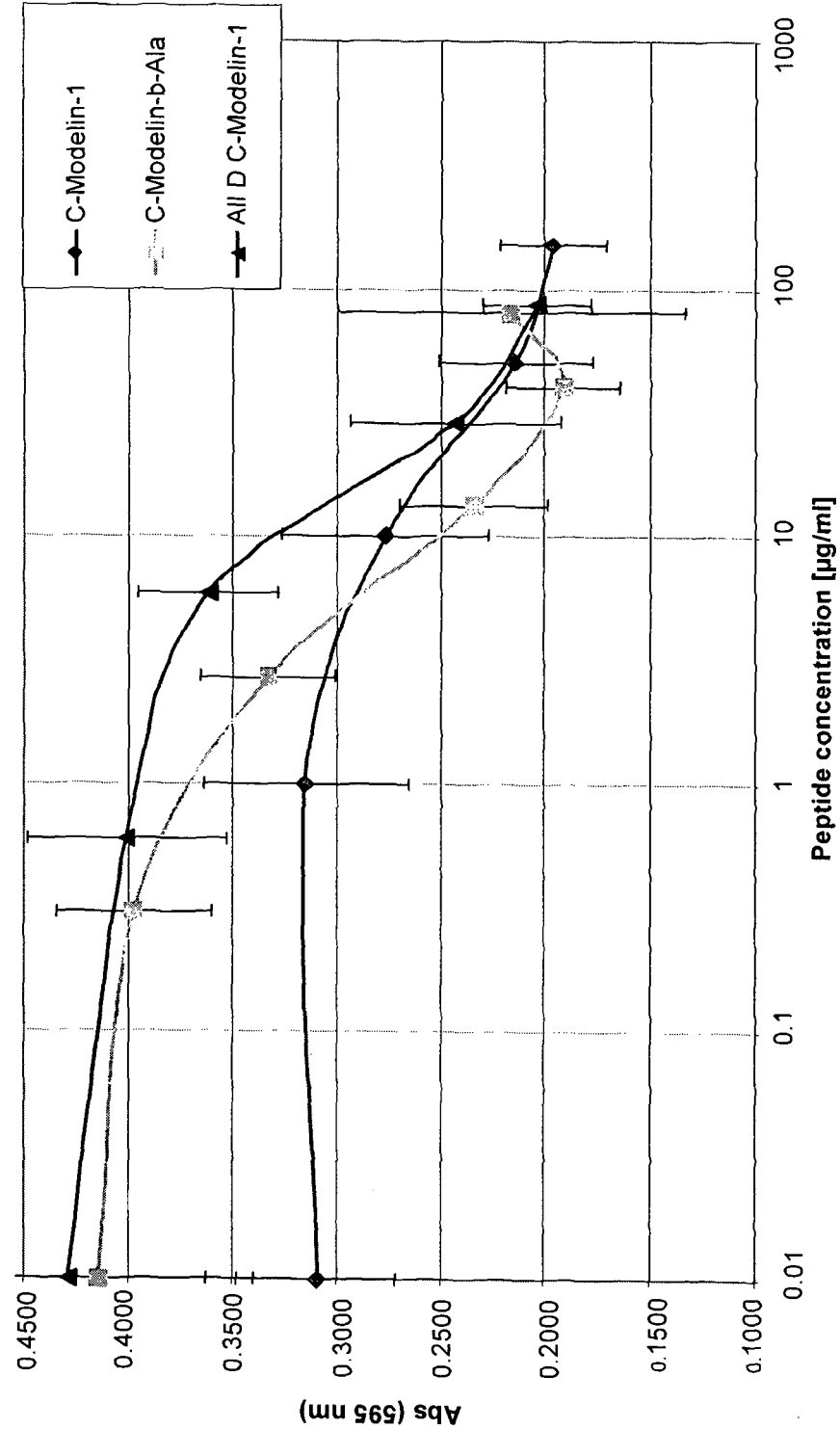
FIG. 1 represents the ABS (595 nm) versus concentration for different types of peptides.

According to preferred embodiments of the invention, the membrane is selected from thin film composite (TFC) membranes, cellulose acetate membranes, other esters of cellulose, ultrafiltration membranes such as polyethersulfone (PES), polysulfones, chlorinated polyvinyl chloride (PVC) or polyvinylidene fluoride (PVDF).

The term "thin film composite (TFC) membrane" defines a semi-permeable membrane composed of a polymer constructed in the form of a film from two or more layered materials. TFC membranes, sometimes termed TFM, are mainly used in water purification or water desalination systems (in reverse osmosis (RO), nanofiltration (NF) and ultrafiltration (UF) applications) but are also used in chemical applications such as batteries and fuel cells.

TFC membranes for RO and NF applications may be prepared from polyethyleneimine/toluene-diisocyanate, polyepiamine, polypiperazine-amide, polypiperazine-trimesamide and many others [see a review: Petersen, R. J. Journal of Membrane Science 83, 81-150 (1993)]. The most common TFC membrane for RO and NF membranes is an aromatic polyamide membrane, namely that the outer film is made of an aromatic polyamide and therefore has free carboxylic groups attached to it. These carboxylic groups can then link directly to a peptide via its amine side to form amide bonds, or it can be used to attach other chemical groups to it, so as to enable covalently attaching a peptide or a tether linked to a peptide, thereto.

The most common TFC membrane for Ultrafiltration (UF) membranes is a polysulfone or polyethersulfone membrane, namely that the outer film is made of a polysulfone. A peptide or a tether can be attached to polyethersulfone UF membrane according to the present invention by initially performing redox-initiated graft co-polymerization with methacrylic acid/PEGMA on the polyethersulfone membrane, as described in Scheme 7. Graft polymerization of UF polyethersulfone membranes was previously done [Belfer S, Fainchtain R, Purinson Y, Kedem O. *Journal of Membrane Science* 172 Issue 1-2 Pages: 113-124]. After graft polymerization, immobilization on the UF membrane may proceed according to the multivalent immobilization in scheme 8 or more efficiently in Scheme 9.

Other UF membranes that peptides can be immobilized are polyacrylonitrile (PAN) UF membrane; Graft polymerization of UF polyacrylonitrile membranes was previously done in our department by S. Belfer [S. Belfer. REACTIVE & FUNCTIONAL POLYMERS 54, Pages: 155-165].

Cellulose Acetate membranes may also be used in the present invention.

The term "antimicrobial peptide" includes both naturally occurring and synthetic peptides, having an antimicrobial activity, which is the ability to prevent, inhibit, reduce or destroy one or more microorganism.

In particular, the present invention includes peptides having an antimicrobial activity against microorganisms causing the formation of biofouling or biofilm formation.

Thus, antimicrobial peptides suitable for the present invention are preferably those that have the ability to prevent, inhibit, reduce or destroy biofilm-forming microorganisms.

The term "microorganism" as used herein refers to bacteria (Gram-positive or Gram-negative), fungi, alga or protozoa. Therefore, biofilm-forming microorganism include bacteria, yeast, fungi and alga and protozoa that are capable of forming biofilm or of causing biofouling.

The term "biofilm" refers to biological films that develop and persist at interfaces in aqueous environments. Biofilm forms when bacteria adhere to surfaces in moist environments by excreting a slimy, glue-like substance made of sugary molecular strands, collectively termed "extracellular polymeric substances" or "EPS."

Biofilm-forming bacteria include, but are not limited to, *Listeria, Salmonella, Campylobacter, Escherichia coli, Pseudomonas*, lactic acid-producing bacteria, *Enterobacteria, Klebsiella* species, *Citrobacteria, Streptococcus, Rodococcus, Bacilus* etc.

The antimicrobial activity of a peptide against a biofilm-forming microorganism can be determined by a method depending on the specific film-forming microorganism in question, and is typically provided as an $IC_{50}$ value.

The term "$IC_{50}$" refers to the concentration of a compound (in this case the antimicrobial peptide) needed to reduce biofilm growth or accumulation of certain microorganism by 50% in vitro or in situ.

The $IC_{50}$ is determined by an essay, suitable for the specific film-forming microorganism in question. For example, in the present invention, the *Enterobacter* assay, which is described in detail in the methods section below, was used to determine the antimicrobial activities of the tested peptides.

The antimicrobial peptides suitable for the present invention are characterized by an $IC_{50}$ against at least one species of biofilm-forming microorganism, of up to 200 µg/ml, preferably of up to 150 µg/ml, more preferably of up to 100 µg/ml and most preferably of up to 50 µg/ml.

As can be seen in Table 7, the antimicrobial peptides of the present invention had $IC_{50}$ values as low as 10-11 µg/ml (for All D C-Modelin-1 and C-Modelin-1, respectively) and even 4 µg/ml (for C-Modelin-1-βAla) to the film-forming *Enterobacter*, under the assay described in 96-microtitter plates (see Experimental section hereinbelow).

Furthermore, as seen in Example 3 below, a PEGylated peptide (HS-PEG-D-Modelin-1) was prepared, and was found to have an $IC_{50}$ as low as 0.4-0.62 µg/ml, much lower than the D-Modelin-1. This means that the PEG tether increased the antimicrobial effect of peptide D-Modelin-1.

Naturally occurring antimicrobial peptides have been isolated from biological sources such as bacteria, insects, amphibians and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, Biopolymers 37:105-122 (1995); Alvarez-Bravo et al., Biochem. J. 302:535-538 (1994); Bessalle et al., FEBS 274:151-155 (1990); and Blondelle and Hougliten in Bristol (Ed.), Annual Reports in Medicinal Chemistry pages 159-168 Academic Press, San Diego and Zasloff M. Nature 415:389-395 (2002), each of which is herein incorporated by reference).

According to some embodiments of the invention, AMPs taken from marine animal species are used.

An antimicrobial peptide can also be an analog or derivative of a natural peptide.

Some suitable derivatives of natural antimicrobial peptides include peptides composed of the methyl-derivatives of the respective amino acids comprising the peptide, or the D-derivatives of these amino acids.

For example, it has been shown by the inventors (see Example 1 below) that all-(D)-amino acid analogs of natural peptides, N-methyl peptides and peptides containing unnatural amino acids in the C-terminal were stable against proteolysis and are therefore preferred peptides for use in the present invention. This is especially important as during biofilm formation, bacteria excrete proteases which may degrade the peptides and therefore it is advantageous that the antimicrobial peptides are also resistant to proteolysis.

Resistance to proteolysis can be determined according to trypsin, chymotrypsin or pronase E assay, as detailed below in the Methods section, namely by adding to each 90 µl of peptide solution, 10 μl of enzyme solution, containing either a mixture of 0.5 μg trypsin (0.05 mg/ml) and 0.5 μg chymotrypsin (0.05 mg/ml) or 4 μg pronase E (0.4 mg/ml) in 0.001M HCl. The enzymatic degradation of the peptide is monitored at controlled temperature of 25° C. A peptide can be considered to be resistant to proteolysis if it withstands this assay for at least 1 week, maintaining at least 90% of its initial concentration after this period.

As can be seen in Example 1 below that the all-D-C-Modelin-1 peptide remained stable over 2 weeks when treated with the proteolytic enzymes.

Thus, according to a preferred embodiment of the present invention, there is provided an antimicrobial water treatment membrane comprising a water treatment membrane, covalently attached to one or more antimicrobial peptides or derivatives thereof via one or more tether molecules, wherein the antimicrobial peptide:
  has an $IC_{50}$ value of up to 200 μg/ml against at least one biofilm-forming microorganism, and
  is stable against proteolysis for at least 1 week.

The term "covalently attached" as used herein, generally refers to an attachment of one molecular moiety to another molecular moiety through covalent chemical bonds. This term does not exclude the existence of other levels of chemical and/or physical bonding, such as hydrophobic bonds, hydrogen-hydrogen bonds etc, in addition to the existence of covalent bonding. Furthermore, the term "covalently attached" may also include strong complex-ligand attachment, as long as it is stable in aqueous conditions such as Avidin/biotin complexation.

Examples of suitable covalent bonds that may form between the membrane and the peptide, or between the membrane and the tether, or between the tether and the peptide include, but are not limited to:
  an amide bond: R—CO—NH—R';
  a thioether bond: R—S—$CH_2$—R';
  a carbon-carbon covalent bond: C—C; and
  a carbon-nitrogen bond: $CR_2$—NH—$CR'_2$—

Additional possible bonds include an azide-alkyne bond, a hydrazine-aldehyde bond, and an Avidin-biotin (host-guest) complexation.

For example if the membrane is a polyamide and has free carboxyl groups which attach directly with the N-terminal side of a peptide, the covalent bond between them would be an amide bond. A similar bond forms between a polyamide membrane and a tether having an amine terminal group.

If however, the membrane or tether linked to it, are attached to a maleimide (MI) molecule, which then attaches to a thiol group on the tether or on the peptide, a covalent thioether bond is formed.

Thus, according to additional embodiments of the invention, the AMP is intentionally modified to include a thiol group as a terminal group. Preferably, this is conducted by adding a Cysteine (Cys) residue, at the AMP amino terminal. Additional modifications include using an all-D peptide or adding a linking group, such as maleimine (MI) to the AMP. These and other modifications are included in the scope of the term "modified peptide", as used herein and may be referred to as peptide derivatives.

A combination of AMPs may also be used.

Since some water purification applications involve saline environments, for example in desalination applications, it is necessary that the antimicrobial peptides shall retain their activity under such conditions. Therefore, according to additional embodiments of the invention, peptides that are microbicidally active in high concentrations of salt are used. The term "microbicidally active" as used herein, refers to a peptide having an $IC_{50}$ of up to 200 μg/ml, preferably up to 150 μg/ml, more preferably of up to 100 μg/ml and most preferably of up to 50 μg/ml against at least one species of biofilm-forming microorganisms.

The term "high concentrations of salt" as used herein refers to a concentration of 3% NaCl. Examples of suitable AMPs for use in saline environments include, but are not limited to, a modified Modelin-1 peptide and a modified Hexpeptide-4.

It has been found by the inventors that although the AMPs can be attached directly to the water treatment membranes, they are preferably attached to it via a tether molecule. Without being bound to a specific theory, it is thought that the tether allows a degree of freedom and movement to the peptides, such that contact with the microorganism (for example, the bacteria) is enabled and creates a "brush" effect that increases its efficiency against biofilm forming microorganisms. For this reason the tether should also help position the peptide relative to the membrane, mainly to maintain a distance between the peptide and membrane surface.

Thus, according to a preferred embodiment there is provided an antimicrobial water treatment membrane comprising a water treatment membrane, covalently attached to one or more antimicrobial peptides or derivatives thereof via one or more tether molecules.

The term "tether" as used herein, is used interchangeably with the terms "spacer" or "arm" and refers to a typically long molecule, such as oligomer or polymer, that is covalently attached to, and interposed between the peptide, or a linker attached thereto, and the membrane substrate or a linker attached thereto, as an alternative to direct attachment between the peptide and the membrane.

Therefore, the tether molecule is typically a molecule such as an oligomer or polymer, having a molecular weight (MW) of at least 300 grams/mol, but more preferably its molecular weight is higher, namely at least 500 grams/mol. Many useful tethers are found in the range of 500-2000 grams/mol. For example, it can be seen that the tethers used in the Examples section below included a long PEG arm, for example, such as PEG-diamine 2000 as well as PEG-diamines of between 800-7500 gr/mol may be used. According to another embodiment the tether includes a Jeffamine™ arm, typically, Jeffamine 300, Jeffamine 500, or Jeffamine 800.

It has been further found that it is preferable that the tether forms a minimal distance between the membrane and the AMP. This minimal distance can be correlated to a maximal, or extended, length of the tether, in an aqueous solution environment being at least 1.5 nanometers long, more preferably at least 3 nanometers long, yet more preferably at least 5 nanometers long.

The term "extended length" (EL) refers to the theoretical maximal length of the polymer, in its stretched form, under aqueous conditions. It is calculated by molecular dynamics calculations.

For example, in the systems prepared in the Examples below, the calculated extended length was 27.3 nm for using PEG3000-diamine tether, 18.2 nm for using PEG2000-diamine tether, 5.1 nm for JeffAmine-800 tether, 3.2 nm for JeffAmine-500 tether, 1.92 nm for JeffAmine-300 tether.

Yet further, it has been found that the ratio between the molecular weight and the extended (maximal) length of the tether, namely MW/EL, is preferably lower than 1,200 grams/mol per 1 nanometer.

For example, in the systems prepared in the Examples below, the calculated ratio between the molecular weight and the extended length was 172 grams/mol per 1 nm for the JeffAmine tether and ~120 grams/mol per 1 nm for the PEG tethers.

On the other hand, most proteins have a ratio of about 7,200 grams/mol per 1 nm, and are therefore less suitable for the purpose of the present invention.

Thus, according to a preferred embodiment of the present invention, there is provided an antimicrobial water treatment membrane comprising a water treatment membrane, covalently attached to one or more antimicrobial peptides or derivatives thereof via one or more tether molecules, wherein this tether:

- is an oligomer or a polymer having a molecular weight (MW) of at least 300 grams/mol,
- has an extended length (EL), in an aqueous environment, of at least 1.5 nanometers; and
- has a ratio between said MW and said EL which is lower than 1,200 grams/mol per 1 nanometer.

While in most cases tethers are synthetic polymers, they can also be bio-polymers, such as DNA, polysaccharides (and oligosaccharides), RNA, etc.

Examples of suitable tether polymers include, but are not limited to, Poly Ethylene Glycol (PEG), poly-acrylamide, poly-(D)-lysine, poly-methacrylic acid, or a co-polymer of methacrylic acid and other acrylate monomer, diamine polymers such as JeffAmine™, poly-maleic anhydride or copolymer of (ethylene) and (maleic anhydride), a lysine dendrimer or any other dendrimer and polyethyleneimine.

Furthermore, the tether molecule must have at least two terminal groups which are capable of linking to at least one peptide on one side and to the membrane on the other side, and the membrane and peptide must also have at least one such group each.

Thus, according to preferred embodiments of the invention, the tether should have at least two terminating groups, each being independently selected from a maleimide (MI) group, 6-aminohexanoic acid, a thiol group, an azide group, an amine group, a carboxyl group or an acetylene group.

Similarly, according to preferred embodiments of the invention, both the membrane and the peptide should also independently have at least one terminating group being selected from a maleimide (MI) group, 6-aminohexanoic acid, a thiol group, an azide group, an amine group, a carboxyl group or an acetylene group.

As discussed hereinabove, suitable covalent bonding between the tether and the membrane and/or the peptide include an amide bond, a thioether bond, a carbon-carbon covalent bond and a carbon-nitrogen bond. Therefore, some examples of suitable terminal groups include, but are not limited to, carboxyl (CO), amine, thiol and imides. In many examples a diamine tether or an amine-terminated and thiol-terminated tethers were used.

However additional attachment nay be based on other common chemical reactions. For example:

Click chemistry, which means coupling of azide group on one site, to an alkyne group on a second site (this method is applicable to membranes that are resistant to organic solvents, since it is performed in solvents such as toluence, tetrahydrofuran, dimethyl-sulfoxide, etc.).

"HydraLink": It is based on a reaction between hydrazine and aldehyde: 2-hydrazinopyridyl moiety on one site, and a benzaldehyde moiety on second site.

Avidin/biotin: a ligation between biotin group (see draw) and avidin. Avidin is a protein which can be bound either via its amine or carboxyl groups. Biotin can be bound via its carboxyl group.

In all of these cases, the tether and/or membrane and/or peptide can be easily modified, mostly "off membrane" to introduce the suitable terminating groups into their respective positions, as known to a person skilled in the art.

The tethers may also be multivalent molecules, such as polymers prepared by graft polymerization or branched polymers have a multitude of functional groups, to which the peptides or linkers may be later attached. Multivalent tethers are advantageous in that they provide a locally-peptide-rich environment in the final product due to high peptide loading on the membrane surface.

According to one preferred embodiment, specific linking groups are used to attach the tether to the AMP and/or to attach the tether to the membrane and/or to attach the AMP to the membrane, and to provide the required regio-selectivity of binding of the antimicrobial peptide. Hence, in many cases, it is advisable that the peptide is linked via a specific site on the peptide chain, usually, but not necessary, near its N-terminal.

The term "linker" is also referred to interchangeably by the term "linking group" or "binding group" and is typically a small molecule containing a suitable binding group. However, the term also encompasses the binding group itself as a chemical group. Some preferable examples of suitable linkers include, but are not limited to molecules including a maleimide (MI) group, 6-aminohexanoic acid, amine, thiol, or azide. Furthermore, suitable linkers may contain an acetylene group to allow, for example, "click chemistry" attachment.

It should be noted that a modified tether, such as a tether attached to a linking group or binding group, as described herein, will typically remain a "tether" as per the definitions provided hereinabove. For example, a PEG tether attached to an MI linker is also defined as a tether for the purpose of this invention, since it remains a polymer or oligomer, having the minimal molecular weight (MW) of 300 grams/mol, as long as it still follows the requirements of a minimal extended length (EL) and a maximal MW/EL ratio.

Thus, it should be also clarified that the polymers or oligomers comprising the tether may be homopolymers and copolymers of all sorts, and may include blocks of oligomers and/or or blocks of polymers linked by one or more linking groups, as suggested herein.

Some additional preferred embodiments of the invention include the following specific antimicrobial water treatment membranes, prepared by the inventors as described herein, having structures I-IV shown below, wherein for each structure j, k, l, m and n are integers independently chosen to be larger than 1, and the peptide is selected from hexapeptide-4, Modelin-1 and All-D-Modelin-1.

I

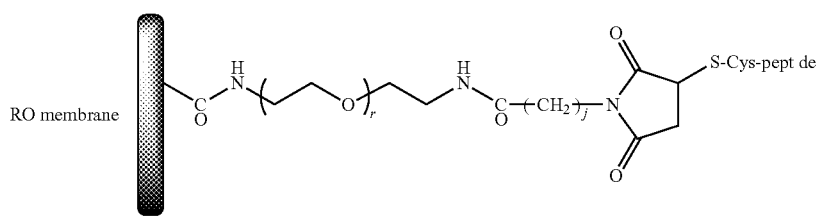

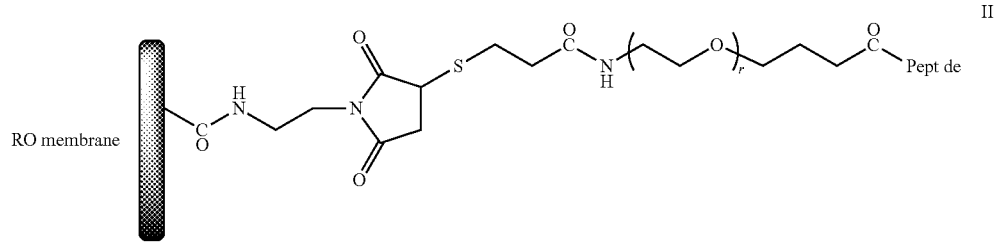

II

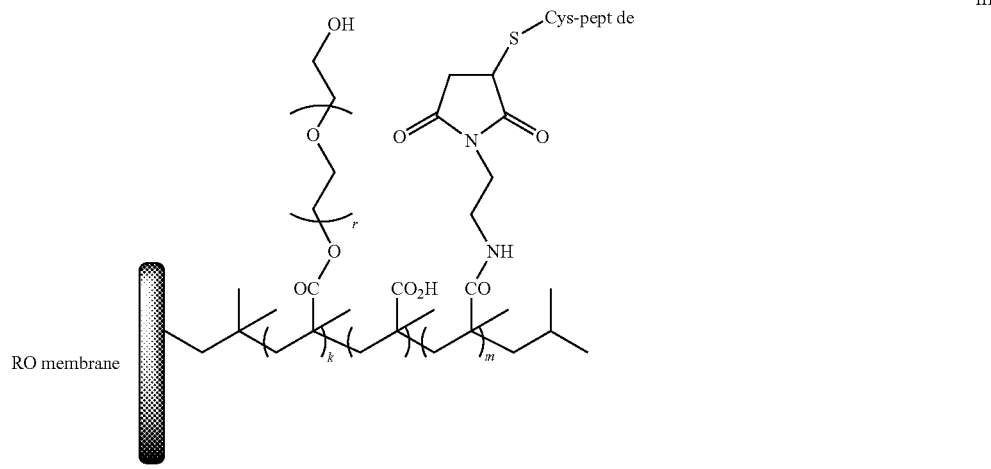

III

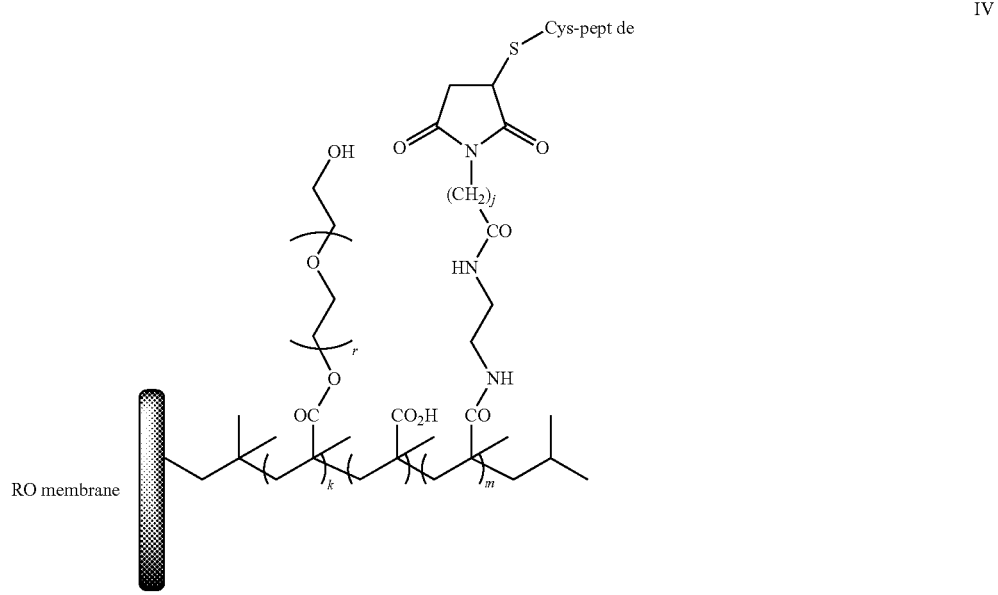

IV

As can be seen in the experimental section which follows, RO membranes having AMPs immobilized thereon via long chain tethers showed reduced biofilm formation on the membrane surface in comparison with membranes not having immobilized AMPs.

Hence, the present invention provides novel membranes and a method for water treatment processes using these AMP immobilized membrane to avoid biofouling during water treatment processes.

As noted above, the one or more antimicrobial peptides were covalently attached to the membrane, either directly or via a tether and/or linker molecules to obtain the antimicrobial membranes described herein.

Thus, according to an additional aspect of the invention, there is provided a process for preparing an antimicrobial water treatment membrane, this process comprising covalently attaching one or more antimicrobial peptides or derivatives thereof to a water treatment membrane, either directly or via a tether molecule.

In particular, since it has been shown by the inventors that the attachment of the peptide to the membrane is done via a tether, there is provided a process for preparing an antimicrobial water treatment membrane, this process comprising covalently attaching one or more antimicrobial peptides or derivatives thereof to a water treatment membrane, via a tether molecule.

The tether and the peptide are as defined hereinabove.

The linking of the peptide to the linker or tether molecules can be via the amine side of the peptide (N-terminus), or via the carboxyl side thereof (C-terminus) or via a side chain. However, preferably, due to ease of preparation, the peptide shall be linked to the tether or linker at its N-terminus. Most preferably, via the thiol group of a cysteine amino acid linked to the N-terminus. This thiol group can be natural or can be synthetically added to the N-terminus of the peptide via a Cys amino acid or via another modification.

In order to obtain the antimicrobial water treatment membranes of the present invention, there are several synthetic routes, but all are based on covalently attaching one or more antimicrobial peptides to a water treatment membrane, optionally via a tether molecule and/or via a linker attaching the peptide to the tether or/linker or attaching the tether/linker to the membrane surface.

More specifically, as detailed below, the preparation of the modified antibacterial water treatment membranes can be affected by one of several routes, some of which are detailed below:

a) Attaching an antimicrobial peptide (AMP) directly to a water treatment membrane (M) to obtain a (AMP-M) modified antimicrobial membrane;
b) Attaching the tether (T) to a water treatment membrane (M) to obtain a membrane-tether (M-T) moiety, and then attaching the antimicrobial peptide (AMP) to the membrane-tether moiety to obtain a (AMP-T-M) modified antimicrobial membrane;
c) Attaching an antimicrobial peptide (AMP) to a linker group (L) to obtain a peptide-linker (AMP-L) moiety and then attaching the linker-peptide moiety to the membrane (M) to obtain a (AMP-L-M) modified antimicrobial membrane;
d) Attaching an antimicrobial peptide (AMP) to a linker (L) to obtain a peptide-linker (AMP-L) moiety, then attaching it to a tether (T) to obtain a peptide-linker-tether (AMP-L-T) moiety, and then attaching this moiety to a water treatment membrane to obtain a (AMP-L-T-M) modified antimicrobial membrane;
e) Attaching the antimicrobial peptide (AMP) to a linker (L) to obtain a peptide-linker (AMP-L) moiety, while separately attaching a tether (T) to a water treatment membrane (M) to obtain a membrane-tether moiety (M-T), and then attaching the peptide-linker moiety to the membrane-tether moiety to obtain a (AMP-L-T-M) modified antimicrobial membrane;
f) Attaching the tether (T) to a water treatment membrane (M) to obtain a membrane-tether (M-T) moiety, then attaching a linker (L) to the membrane-tether moiety to obtain a membrane-tether-linker (M-T-L) moiety, and then attaching the antimicrobial peptide (AMP) to the membrane-tether-linker moiety to obtain a (AMP-L-T-M) modified antimicrobial membrane; or
g) Attaching a linker (L) to a water treatment membrane (M) to obtain a membrane-linker (M-L) moiety, then attaching a tether (T) to the membrane-linker moiety to obtain a membrane-linker-tether (M-L-T) moiety, then attaching it via another linker (L) to an antimicrobial peptide (AMP) to obtain a (AMP-L-T-L-M) modified antimicrobial membrane.

In each of this cases the linker may be linear or branched, and the tether may be single valent or multivalent.

For further clarity, it should be emphasized that the moiety AMP-L can be regarded as a modified peptide, that the moiety M-L can be regarded as a modified membrane, that the moiety T-L can be regarded as a modified tether and that the moiety T-AMP can be defined as a tethered AMP.

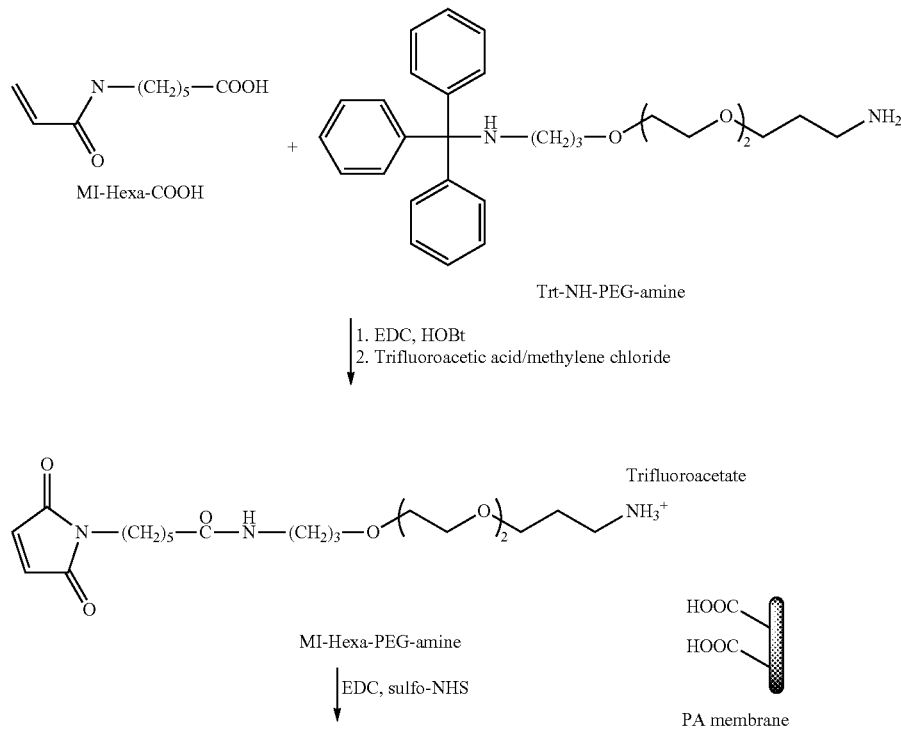

Scheme 1 (AMP-L-T-M)

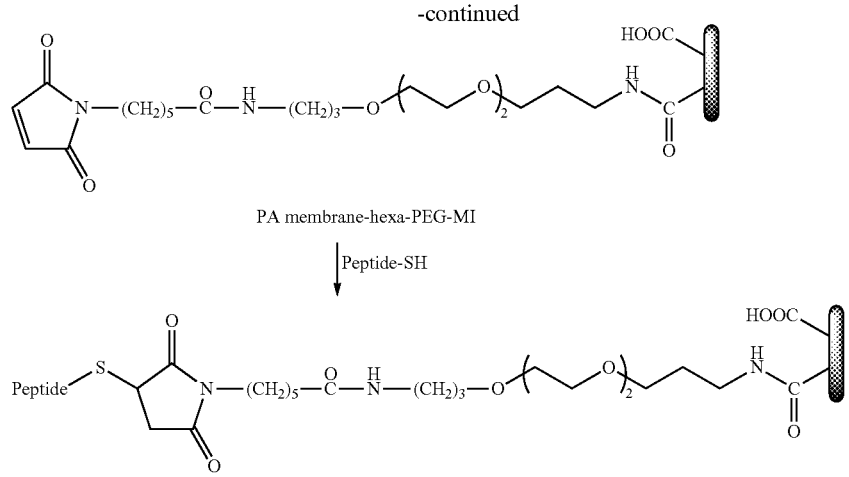

PA membrane-hexa-PEG-MI

↓ Peptide-SH

Scheme 1 illustrates an exemplary scheme of covalent binding of AMPs to an RO-polyamide membrane surface. In this scheme, AMPs are attached to an aromatic polyamide (PA) RO membrane through a thiol-binding group which binds an Maleimide (MI) linker bound to PEG-amine tether that is attached to the membrane. In the method exemplified in Scheme 1, the step of attaching a protected PEG-amine tether to an MI linker is preformed prior to attachment to the membrane ("off membrane"). The linker-PEG-amine molecule is then attached to the membrane by the use of coupling reagents, so that the linker is free to bind an AMP in a subsequent step. An AMP having a thiol-binding group is then attached to the linker-PEG amine tether-membrane. Both steps of attaching the linker-PEG-amine tether to the membrane and attaching the AMP to the linker-PEG amine-tether, are done on the membrane.

Schemes 2A and 2B show another exemplary attachment of peptides to a tethered RO membrane.

Scheme 2A

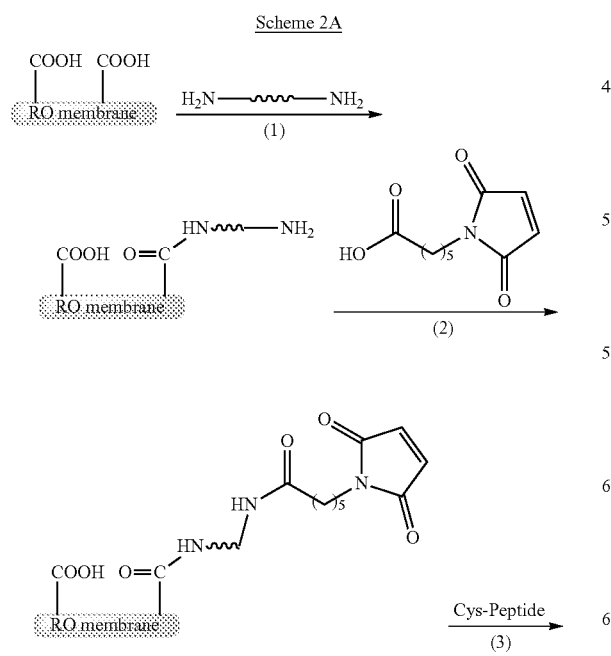

-continued

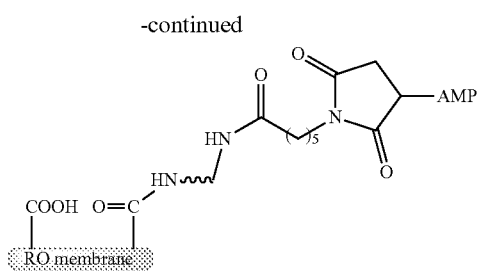

Scheme 2B (AMP-L-T-M)

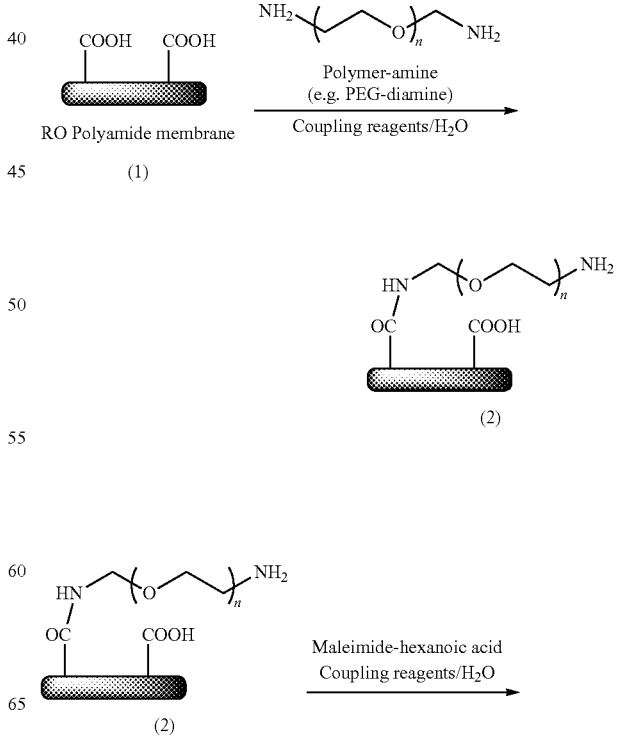

maleimide linker is used in the 1st step, and PEG-peptide is used in the second step.

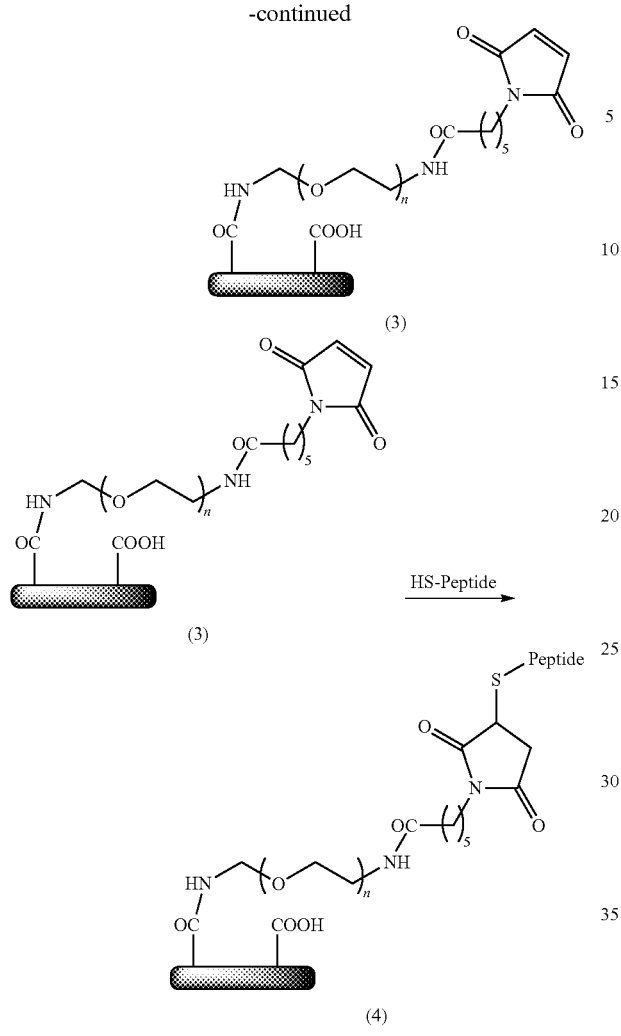

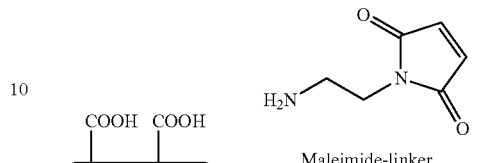

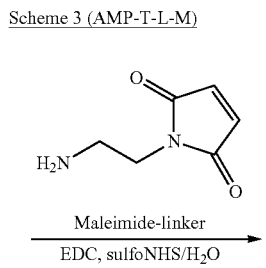

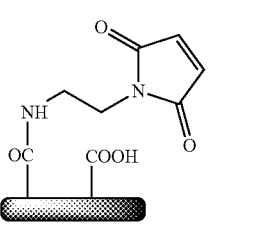

Scheme 3 (AMP-T-L-M)

Schemes 2A and 2B show a three-steps process for modifying the membrane: "off membrane", an SH (thiol) group is added to the peptide to obtain a SH-peptide. Then, a di-amine polymer tether is attached to the membrane in the presence of coupling reagents. The tether is a polymer, and in many cases is chosen to be a long Jeffamine™ arm or a PEG-diamine molecule, as shown in the scheme. Examples of coupling reagents include 1-ethyl-3-(3-(dimethylamino)propyl) carbodiimide hydrochloride (EDC) and N-hydroxy-sulfosuccinimide (sulfoNHS).

A linker, such as MI-hexanoic acid molecule is then attached to the immobilized tether, in the presence of coupling reagents. A peptide is then attached to the linker via the thiol group of the peptide C-terminal cysteine. The MI group on the tether-membrane then reacts with the thiol group on an antibacterial peptide, typically with the thiol on the cystein residue at the N-terminus of the peptide. The MI-cys reaction is carried out without coupling reagents but in the presence of nitrogen, or oxygen free atmosphere, so as to keep an inert environment, to prevent oxidation of the cystein residue and increase the yield; however, the process can be carried out under atmospheric conditions as well.

Schemes 3 and 4 show another type of immobilization process to obtain a Membrane-linker-tether-peptide system. One example is shown in Scheme 3, which presents an efficient 2-steps synthesis on the membrane, whereas amine- As can be seen in Scheme 3, a thiol-tether-peptide (thiol-PEG-all-D-Modelin-1) was synthesized first. The synthesis of thiol-PEG-D-Modelin-1 was performed on solid support (SPPS), and was successful according to the HPLC and MS analyses of the thiol-PEG-D-Modelin-1 product.

Scheme 4 shows another exemplary alternative attachment of peptides to an RO membrane to obtain a membrane-linker-tether-peptide system, having a branched linker.

According to this embodiment a linker (such as maleimide) is attached via a small molecule (such as 2-amino-ethyl-maleimide) to the membrane. Branched linkers may be used during this step (for example Bis-Mal-Oc-$NH_2$ in Scheme 3). Other branched linkers, such as commercially available dendrimers with appropriate end groups, may be used. The use of branched linkers may enhance AMP concentration on the membrane. A peptide is attached to a tether (such as a PEG molecule) off-membrane. Typically, the tether has a binding group (e.g., thiol) at its end to enable attachment to the linker which is immobilized to the membrane. The AMP with a thiol-tether at its N-terminal is then attached to the maleimide on the membrane.

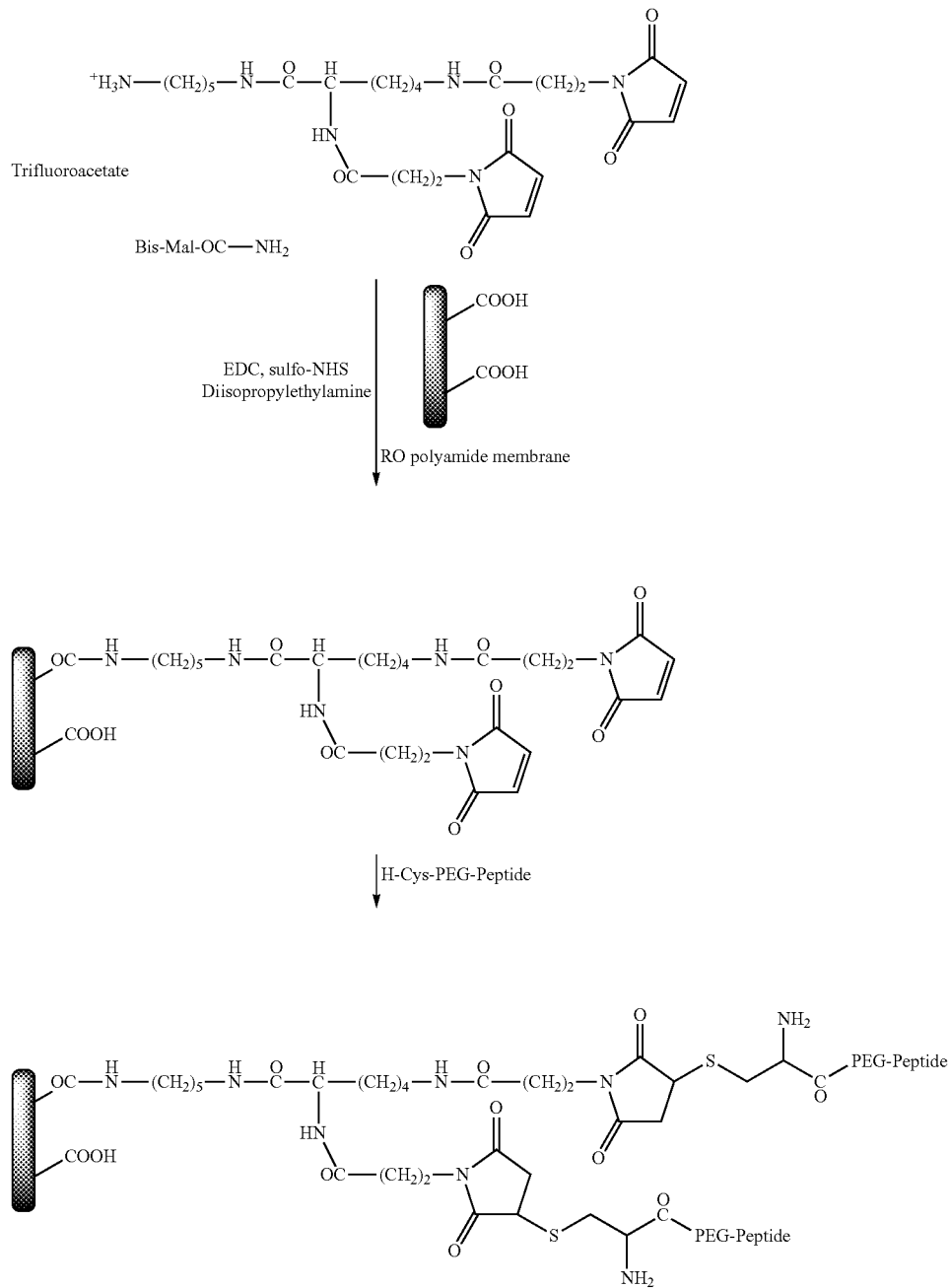

Scheme 4 (AMP-T-branched L-M)

According to other embodiments, instead of maleimide-thiol chemistry the linker may be based on click chemistry, for example, using an acetylene and azide group linkers.

As a high local concentration of the antimicrobial peptides on bacterial membrane is required for the lethal effect of the peptides, an increase of local concentration of the peptides was now achieved by the inventors by multivalent immobilization of AMPs on RO membranes, using two approaches: By graft polymerization, and by dendrimers or multifunctional polymers, as shown in scheme 5, in comparison to linear immobilization.

Scheme 5

Linear Immobilization:

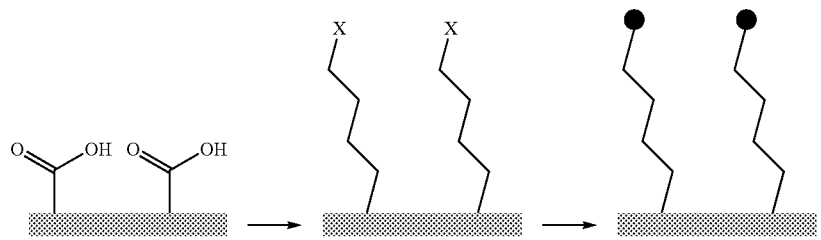

Multivalent Immobilization:

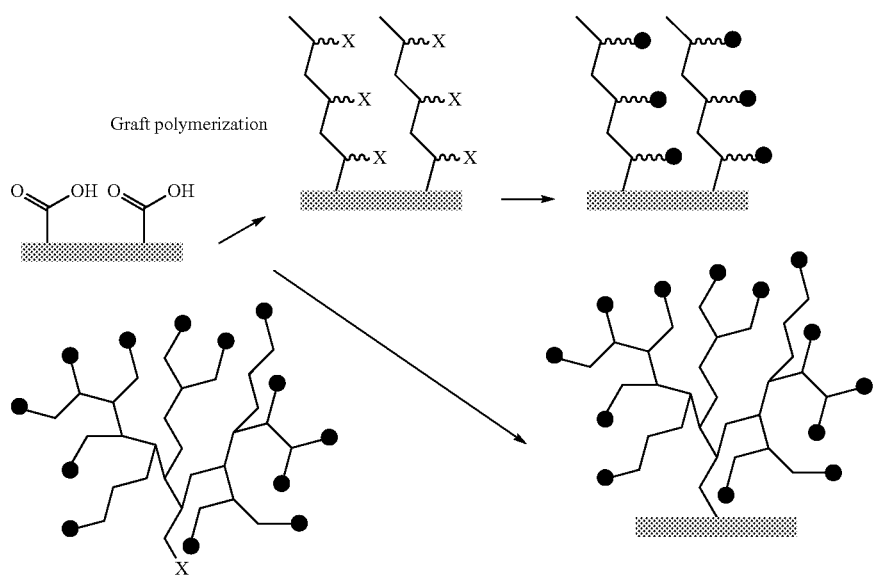

Dendrimers/Multifunctional polymers

● = Peptide

Graft polymerization (e.g., according to the procedure described in Belfer, et al. (1998) Journal of Membrane Science, 139, 175-181) may be used to obtain multi-arms molecular systems on the water treatment membrane, which has multiple copies of a functional group such as carboxyl, amine, thiol, ether or hydroxyl. This system may be used to attach linkers to membranes. Graft polymerization may be used advantageously for attaching linkers to the membrane in a branched manner, hence multiple copies manner.

A large number of monomers can be used in a graft polymerization process whereas the most suitable are commercially available monomers that can be polymerized in aqueous solutions by known procedures, such as acrylate- and methacrylate-derivatives. Preferably, the monomers are selected from the group comprising of acrylate- and methacrylate-derivatives, maleic anhydride, ethylene, ethyleneglycol derivatives vinyl-pyrrolidone, vinyl-derivatives that have carboxyl or amine groups, and styrene derivatives.

Some preferred monomers are listed in Scheme 6 below:

Scheme 6

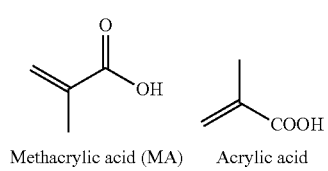

Methacrylic acid (MA)   Acrylic acid

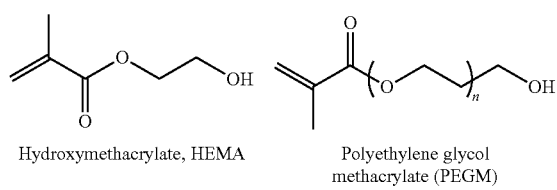

Hydroxymethacrylate, HEMA   Polyethylene glycol methacrylate (PEGM)

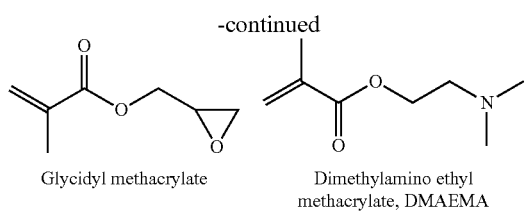

An exemplary graft polymerization process, conducted in situ on an RO polyamide membrane, using the Methacrylic acid (MA) and Polyethylene glycol methacrylate (PEGM) monomers using redox-initiated graft-polymerization technique is depicted in scheme 7 below:

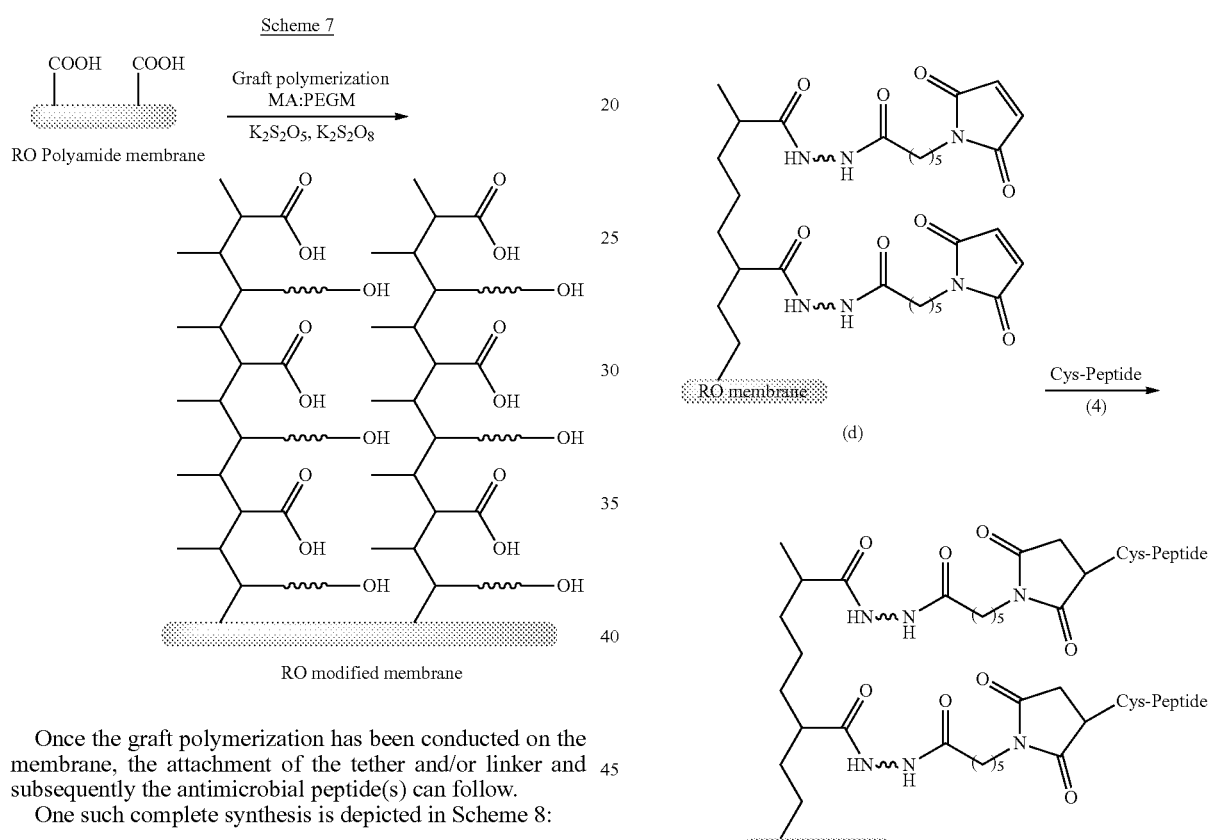

Once the graft polymerization has been conducted on the membrane, the attachment of the tether and/or linker and subsequently the antimicrobial peptide(s) can follow.

One such complete synthesis is depicted in Scheme 8:

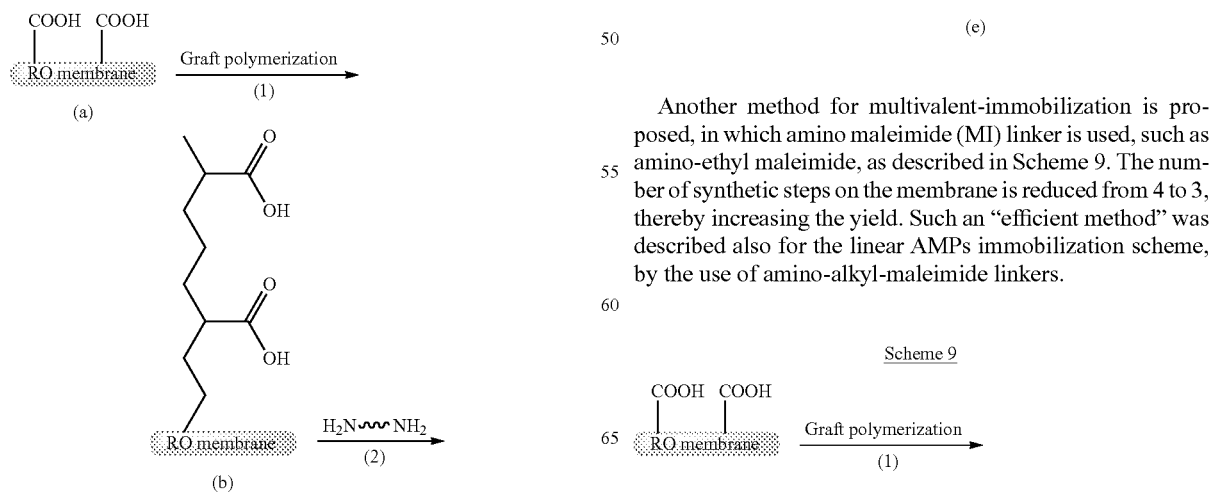

Another method for multivalent-immobilization is proposed, in which amino maleimide (MI) linker is used, such as amino-ethyl maleimide, as described in Scheme 9. The number of synthetic steps on the membrane is reduced from 4 to 3, thereby increasing the yield. Such an "efficient method" was described also for the linear AMPs immobilization scheme, by the use of amino-alkyl-maleimide linkers.

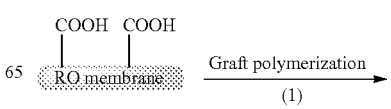

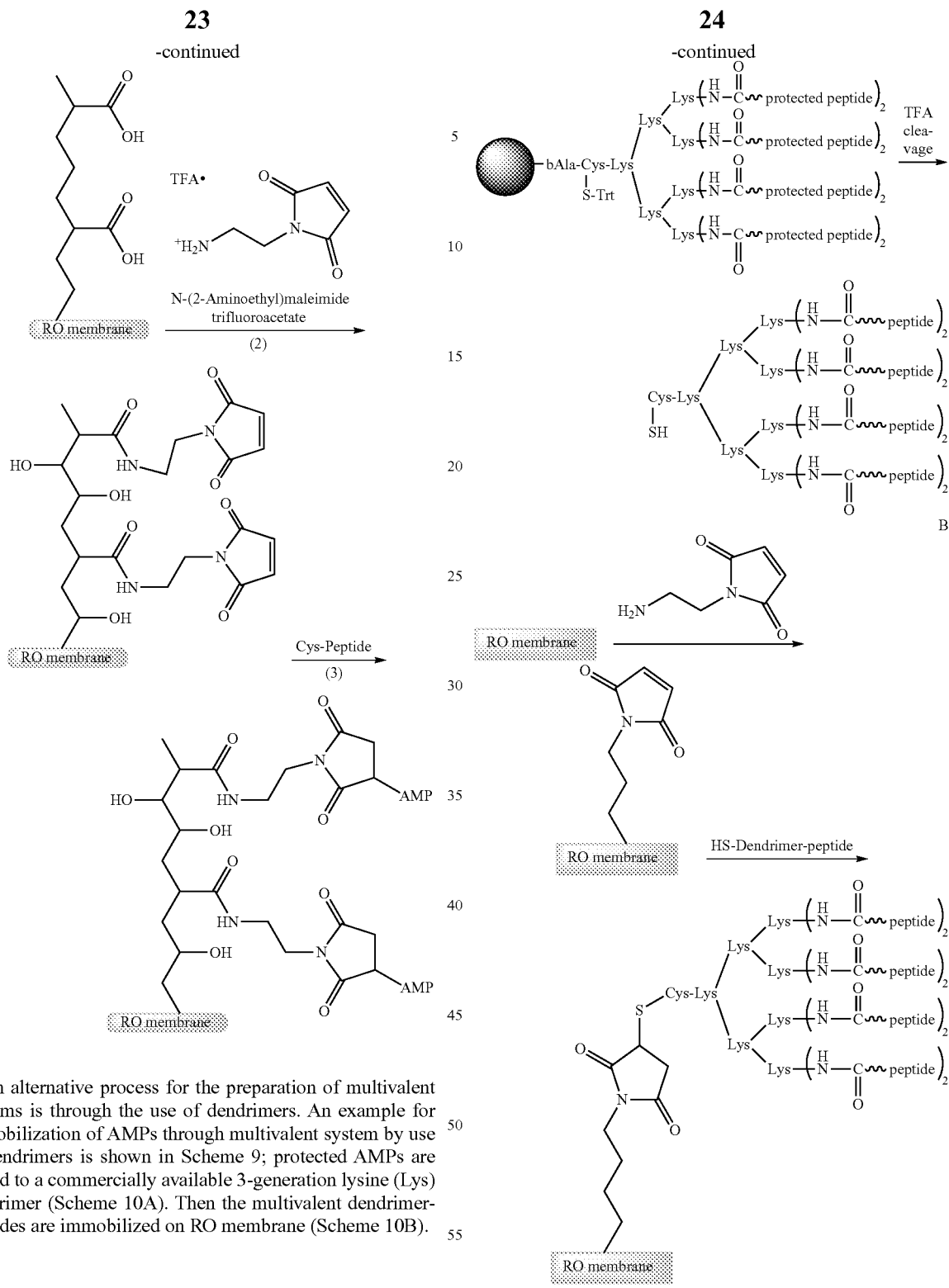

An alternative process for the preparation of multivalent systems is through the use of dendrimers. An example for immobilization of AMPs through multivalent system by use of dendrimers is shown in Scheme 9; protected AMPs are bound to a commercially available 3-generation lysine (Lys) dendrimer (Scheme 10A). Then the multivalent dendrimer-peptides are immobilized on RO membrane (Scheme 10B).

Scheme 10

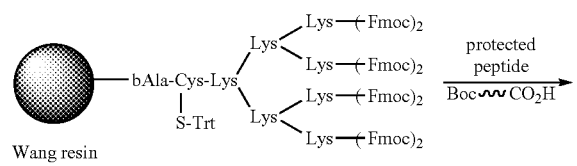

A

Multifunctional polymers may also be used to immobilize peptides to RO membranes in multivalent system. in the first stage a polymer conjugated to multiple copies of an antimicrobial peptide is created. (see Scheme 11 for example, based on Liu, Z. G., et al., J. Med. Chem. (2006); Gestwicki, J. E. et al. JACS, (2002)). In the second stage binding the polymer peptide conjugate to the RO membrane surface is done as was described for dendrimers in Scheme 10B.

Scheme 11

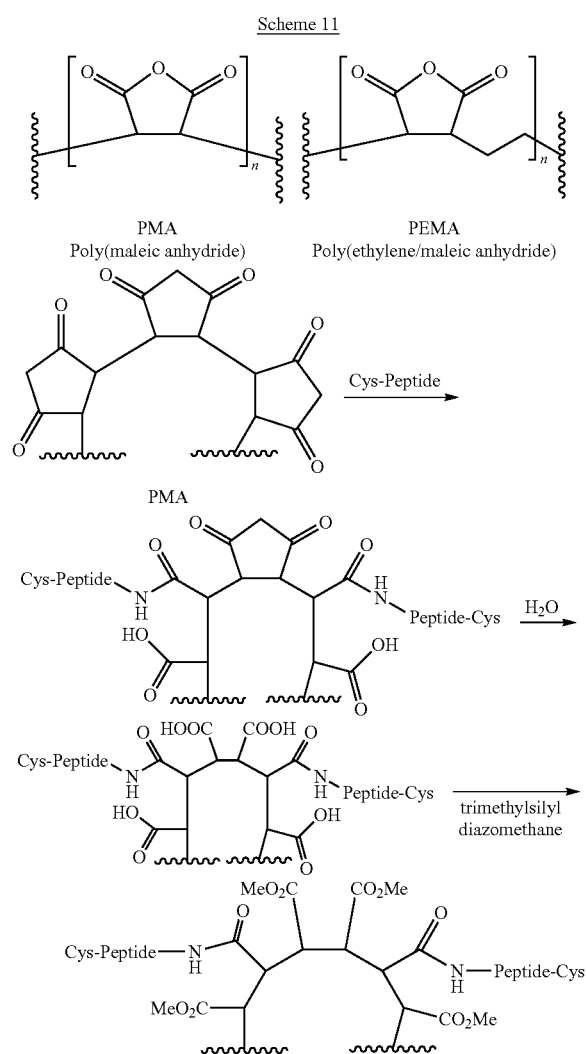

The experimental methods that were described for immobilization of antimicrobial peptides on water treatment membranes represent a novel strategy for coping with biofilm growth on surfaces in water technologies; inhibition of biofilm growth on such surfaces, especially RO and NF membranes, will increase their life time, and eventually will lead to lower costs of water treatment.

Thus, according to another aspect of the invention, there is provided the use of an antimicrobial water treatment membrane in antimicrobial water purification processes comprising sea-water desalination, waste water treatment, brackish water treatment, industrial water treatment and water recycling, wherein the antimicrobial water treatment membrane is the membrane according to the present invention, as described hereinabove.

Furthermore, there is therefore also provided an antimicrobial water purification process, comprising contacting a water source selected from sea-water, waste water, brackish water, industrial water, irrigation water and drinking water, with an antimicrobial water treatment membrane according to the present invention, as described hereinabove.

For more information on membranes for RO, uses and modes of application thereof see: Petersen, R. J. (1993) *Journal of Membrane Science* 83, 81-150; and R. Kasher. Membrane-based water treatment technologies: Recent achievements, and new challenges for a chemist. Bulletin of the Israel Chemical Society|Issue No. 24, December 2009.

For more information on water treatment by membranes, see: Advanced Membrane Technology and Applications. Norman N Li (Editor), Anthony G. Fane (Editor), W. S. Winston Ho (Editor), Takeshi Matsuura (Editor). John Wiley and Sons, New Jersey (2008).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Experimental Section

Reference is now made to the following examples, which together with the above descriptions, illustrate the invention in a non limiting fashion.

Materials

Amino acids used for peptide synthesis (L and D configurations): Fmoc-Ala-OH, Fmoc-D-Ala-OH, Fmoc-Ahx-OH, Fmoc-Arg(Pbf)-OH, Fmoc-Asp(OtBu)-OH, Fmoc-Cys(Trt)-OH, Fmoc-D-Cys(Trt)-OH, Fmoc-Glu(OtBu)-OH, Fmoc-Gly-OH, Fmoc-Ile-OH, Fmoc-Leu-OH, Fmoc-D-Leu-OH, Fmoc-Lys(Boc)-OH, Fmoc-D-Lys(Boc)-OH, Fmoc-Phe-OH, Fmoc-Pro-OH, Fmoc-Trp(Boc)-OH, Fmoc-D-Trp(Boc)-OH. The amino acids were purchased from Advanced ChemTech (Louisville, Ky.), Iris Biotech GmbH (Marktredwitz, Germany), Novabiochem (Laufelfingen, Switzerland) Biosolve (Valkenswaard, The Netherlands), Chem-Impex International (Wood Dale, Ill.).

Resins used for Solid Phase Peptide Synthesis: Rink resin ss, 100-200 mesh, 1% DVB, 0.7 mmol/g; Wang resin ss, 100-200 mesh, 0.6 mmol/g; Fmoc-Trp(Boc)-Wang resin, 100-200 mesh, 0.6 mmol/g, Fmoc-D-Trp(Boc)-Wang resin, 100-200 mesh, 0.6 mmol/g, Fmoc-β-Ala-Wang resin, 100-200 mesh, 0.22 mmol/gr, [Fmoc-Lys(Fmoc)]$_4$-Lys$_2$-Lys-Cys (Acm)-β-Ala-Wang resin, 200-400 mesh, 1.0 mmol(Fmoc)/gr, Fmoc-Asp(Wang resin)-Amc, 100-200 mesh, 0.65 mmol/g. The resins were purchased from: Advanced Chemtech (Louisville, Ky.), Chem-Impex International (Wood Dale, Ill.) and Novabiochem (Hohenbrunn, Germany).

Solvents and Reagents:

N-methyl-pyrrolidone (NMP), N,N'-dimethylformamide (DMF) and dichloromethane (DCM) (peptide synthesis grade) were purchased from J. T. Baker (Pillipsburg, New-Jersey) and Bio-Lab (Jerusalem, Israel). Coupling reagents HBTU, HOBt, PyBOP and DMAP were purchased from Chem-Impex International (Wood Dale, Ill.) and Luxembourg Bio Technologies (Rehovot, Israel). Acetic anhydride, triisopropylsilane, crystal violet, toluidine blue, orange II, HEPES buffer, ethyl-dimethylaminopropyl-carbodiimide (EDC) and 6-maleimidohexanoic acid were purchased from Sigma (st. Louis, Mo.). NHS and AMC were purchased from Chem-Impex International (Wood Dale, Ill.). DIEA was purchased from Advanced ChemTech (Louisville, Ky.). Piperidine, dicyclohexylcarb 3 odiimide (DCC), trifluoroacetic acid, pyridine, tert-butyl methyl ether, ethanol, toluene, acetone, acetonitrile and isopropanol were purchased from Bio-Lab (Jerusalem, Israel). 1,2-ethanedithiol was purchased from Acros Organics (Geel, Belgium). Ninhydrin, dithiothreitol and Jeffamine$_{500}$ were purchased from Fluka (Buchs, Switzerland). Diamine $PEG_{2000}$ was purchased from Rapp Polymere (Tubingen, Germany). Glycerol was purchased from Ridel-de Haën (Seelze, Germany). 33EDTA purchased from BDH chemicals Ltd (Pool, England). Poly(maleic anhydride) and poly(ethylene-maleic anhydride) were purchased from Polysciences (Warrindton, Pa.). Trimethylsilyl diazomethane was purchased from TCI (Tokyo, Japan).

The enzymes caspase 8, trypsin (EC 3.4.21.4), chymotrypsin (EC 3.4.21.1) and pronase E (EC 3.4.24.31) were purchased from Sigma (st. Louis, Mo.). TSB was purchased from Acumedia Manufacturers (Lansing, Mich.). RTV 186 was purchased from Polymer G'vulot (Kibbutz G'vulot, Israel).

RO membranes FILMTEC SW30HR LE-400 seawater RO and FILMTEC LE-400 high productivity low-energy brackish water RO were gifted from DOW (Midland, Mich.). ESPA1 RO was gifted from Hydranautics (Oceanside, Calif.).

Apparatus and Analytical Methods

Reversed phase HPLC used for peptide analysis and purification: Analytical RP-HPLC separations were performed on Surveyor quaternary gradient pump, Surveyor dual—wavelength UV/Vis Detector with 50 mm light-pipe flow cell, Surveyor FAST Autosampler (Thermo Fisher Scientific, Waltham, Mass.) equipped with additional manual injector with loop volume of 2 ml (Rheodyne, Rohnert, Calif.) and Gilson FC 203B Fraction collector (Middleton, Wis.). When using eluent flow higher than 4 ml/minutes degassing was performed by He gas bubbling. A 4.6×250 mm C18 column with 5 μm particle size and 110 Å pore size was used (Phenomenex, Torrance, Calif.). Detection wavelength was 220 nm.

The solvents that were used for the mobile phase: solvent A—double distilled water (DDW) with 0.1% TFA and solvent B—75% ACN in DDW with 0.1% TFA. The column was washed with solvent C—65% ACN in DDW. All solvents were filtered (0.22 μm/0.45 μm) before use. For the peptides C-Modelin-1, CX-Modelin-1, C-Modelin-1-βAla, all (D) C-Modelin-1 and Cys-Ile-Glu-Prp-Asp-Amc the elution gradient was: t=0 minutes, B=15%; t=5 minutes, B=15%; t=45 minutes, B=70%; t=47 minutes, B=95%; t=57 minutes, B=95% (flow rate 1 ml/minute). For RWRW, Hexapeptide-4, $CG_3$-Hexapeptide-4 and $CG_4$-Modelin-1 the elution gradient was: t=0 minutes, B=5%; t=5 minutes, B=5%; t=45 minutes, B=95%; t=50 minutes, B=95% (flow rate 1 ml/minute).

Preparative HPLC Separations:

Preparative separations were performed either on the above Surveyor HPLC system, or on RP-HPLC that consists of Waters 600 Semi-Prep HPLC controller and quaternary pump (Milford, Mass.) equipped with manual injector with loop volume of 5 ml (Rheodyne, Rohnert, Calif.), Spectro monitor 3100 UV/vis detector (Milton-Roy, Ivyland, Pa.) and Gilson FC 204 Fraction collector (Middleton, Wis.). For preparative separations the peptides were dissolved in DDW or ACN/DDW solution and filtered before the HPLC separation. A sample (up to 60 mg of peptide) was injected by manual injector port with 2 or 5 ml loop. A 21.2×250 mm C18 column with 10 μm particle size and 300 Å pore size (Phenomenex, Torrance, Calif.) was used for the separations. Flow rate was 8 or 12 ml/minutes. Detection wavelength was 230 nm. Eluents were mixture of solvent A and B (of analytical).

Mass Spectrometry of Synthesized Peptides:

A peptide sample dissolved in 3/1 acetonitrile/water mixture was analyzed by MALDI-TOF mass spectrometry (REFLEX-IV MALDI-TOF mass spectrometer Bruker Daltonics, Bremen, Germany), by Dr. Mark Karpases from the analytical services and instrumentation unit of Ben-Gurion University of the Negev.

ATR-FTIR Spectroscopy and Estimation of Degree of Grafting (DG):

Attenuated total reflection furrier transform infra-red (ATR-FTIR) spectroscopy measurements were recorded on a VERTEX 70/80 standard system spectrophotometer, using a KRS crystal (BRUKER Optiks GmbH, Ettlingen, Germany). The membranes were completely dried overnight in a vacuum desicator prior to the measurement.

Quantitative Biofilm Growth Inhibition Assay in a 96-Wells Microtiter Plate:

*Enterobacter* culture (50 ml) was grown in tryptic soy broth media (TBS; prepared according to manufacturer instructions) overnight at 25° C. On the next day the turbidity of the culture was measured at 600 nm (Biomate 5 UV-Vis spectrophotometer, Thermo Fisher Scientific, Waltham, Mass.) and, if necessary, TSB was added to dilute the culture until the OD was 1.

Then 96 wells polystyrene microtiter plates (flat bottom, transparent, Becton Dickinson, Franklin Lakes, New-Jersey) were filled as following: Negative control wells (without bacteria) were filled with 125 μl TSB media and 25 μl of DDW:PBS1:1 buffer solution; Positive control wells (without peptide solution) were filled with 110 μl TSB media, 25 μl of DDW:PBS1:1 buffer solution and 15 μl of *Enterobacter* culture solution; Wells that contained AMPs at different concentrations were filled with 110 μl TSB media, 25 μl of peptide solution and 15 μl of *Enterobacter* culture solution.

The plates were incubated at 25° C. overnight. On the next day the plates were gently rinsed 5 times with distilled water to remove the planktonic bacteria and then dried at room temperature for 10 minutes. Then the biofilm on the walls of the wells was dyed by adding 200 μl, of 3% crystal violet (CV) to the wells. After 15 minutes at room temperature, the plates were gently rinsed 5 times with distilled water to remove excess dye and dried at room temperature for 10 minutes (Djordjevic, Wiedmann & McLandsborough 2002). The dry plates were filled with 200 μl ethanol, covered and gently agitated (Duomax 1030 rocking platform shaker, Heidolph, Kelheim, Germany) for 1 hour. The absorbance of extracted color was measured in a plate reading spectrophotometer (Infinite M200, Tecan, Mannedorf, Switzerland) at 595 nm.

Toluidine Blue (TB) Test for Membrane Modification Yield (Determination of Carboxylic Groups on RO Membranes):

The test measures the carboxyl group concentration on the surface of the membrane, and was used to estimate the degree of modification. The test was based on the published article by Nakajima et al. 1995 [Nakajima, N. 1995, Bioconjugate chemistry, vol. 6, no. 1, p. 123] with various modification; the membranes were glued to glass slides using RTV 186 glue (prepared according to manufacturer instructions—Polymer G'vulot). Toluidine blue (0.5 mM in NaOH solution, pH=10) was added to the membranes and agitated for 3 hours. The membranes were rinsed with NaOH solution pH=10 until the rinsing solution was completely colorless (normally 8-10 times, 5 minutes each). The dye was eluted with minimal volume (12-13 ml) of 50% (v/v) acetic acid for 2 hours. The absorbance of the dye was measured at 633 nm (Lambda EZ 201 PerkinElmer spectrophotometer, Waltham, Mass.). For reference, a 50% acetic acid solution was used. To determine the surface concentration of carboxyl groups a calibration curve was constructed using the following. TB concentrations (in 50% acetic acid): 5 μM, 4 μM, 3 μM, 2 μM, 1 μM and 0.5

μM. The surface concentration of the acid groups was calculated based on the membrane area, dye concentration, and volume of the eluting solution. The concentration of carboxyl groups on membrane surface was calculated with the assumption of 1:1 dye:carboxyl group complex.

Initially, the concentration of carboxyl groups on the surface of 3 different RO membranes was estimated using Toluidine blue adsorption: ESPA1, FILMTEC SW30HR LE-400, and FILMTEC LE-400 (brackish water). The results are presented in Table 1.

TABLE 1

| RO membrane | Membrane area [$cm^2$] | Absorption (633 nm) | COOH concentration [M] | COOH surface concentration$^a$ [mol/$cm^2$] |
|---|---|---|---|---|
| ESPA1 | 12.0 | 0.850 | $2.28 \times 10^{-5}$ | $2.28 \times 10^{-8}$ |
| FILMTEC LE-400 | 19.8 | 0.534 | $2.86 \times 10^{-5}$ | $1.74 \times 10^{-8}$ |
| FILMTEC SW30HR LE-400 | 12.0 | 0.278 | $7.43 \times 10^{-6}$ | $7.43 \times 10^{-9}$ |

$^a$V = 12 ml

According to the results, ESPA1 membrane had the highest concentration of surface carboxyl groups.

Peptide Loading Determination on Ro Membrane Using a Labile Fluorescent Residue 7-Amino-4-Methylcoumarine (Amc):

For quantitative determination of peptide loading on the membranes surface a model peptide H-Cys-Ile-Glu-Pro-Asp-AMC was used as a substrate for the enzyme caspase 8. Caspase 8 cleaves the amide bond between aspartic acid and AMC and releases free AMC to the solution, where it can be detected by fluorescence spectrophotometer. The model peptide was attached to the RO membrane with different spacers, peptide concentrations and reaction times and its loading was determined by an enzymatic assay.

Peptides having the labile fluorescent group, 7-amino-4-methylcoumarine (AMC), were prepared. H-Cys-Ile-Glu-Pro-Asp-AMC was synthesized by the SPPS method, on a commercially available resin Fmoc-Asp(Wang-resin)-AMC, using standard Fmoc chemistry. The synthesis was carried out automatically, using automated peptide synthesizer. The synthesized peptide was analyzed by RP-HPLC system and its sequence was confirmed by MALDI-TOF MS. The peptide H-Cys-Ile-Glu-Pro-Asp-Amc was immobilized on 2 $cm^2$ RO membranes (previously washed) via diamine $PEG_{2000}$ or $Jeffamine_{500}$, as described above. For the enzymatic cleavage of the Amc label the following buffer solution was prepared: 100 mM HEPES, pH=7.5, 20% (v/v) glycerol, 5 mM dithiothreitol and 0.5 mM EDTA. 40 μl of caspase 8, dissolved in DDW, was added to 1.96 ml of buffer solution and transferred to the peptide immobilized membranes. The membranes were kept in dark and incubated in 31° C. in a ZHWY-1102C incubator shaker (Zhicheng, Shanghai, China) over 7 days during which the fluorescence of the solution was measured in given time intervals (excitation wavelength=380 nm, emission wavelength=460 nm) using Cary eclipse fluorescence spectrophotometer (Varian, Palo Alto, Calif.). The enzymatic reaction was also tracked in a solution that consisted of 120 μl of unbound peptide substrate H-Cys-Ile-Glu-Pro-Asp-Amc (13.3 mM) dissolved in DDW, 40 μl of caspase 8 solution and 1.84 ml of 100 mM HEPES, pH=7.5. The peptide solution was incubated at 31° C. in dark in incubator shaker for 7 days and its fluorescence was measured as membrane solutions.

To determine the surface concentration of immobilized peptides, a calibration curve was constructed using the following free Amc concentrations (in HEPES buffer solution): 0.1 μM, 0.2 μM, 0.4 μM, 0.6 μM 0.8 μM, 1.6 μM, 2.4 μM, 3.2 μM, 4 μM. The surface concentration of the immobilized peptides was calculated based on the membrane area, Amc concentration in solution, and volume of the solution.

Table 2 shows the fluorescence values obtained for the different modification conditions.

TABLE 2

| | Over night reaction | | | | | | 3 hours reaction | |
|---|---|---|---|---|---|---|---|---|
| | PEG 4 mM | Jeff 4 mM | PEG 1 mM | Jeff 1 mM | PEG 0.2 mM | Jeff 0.2 mM | PEG 4 mM | Jeff 4 mM |
| Immobilized peptide surface concentration$^a$ [nmol/$cm^2$] | 0.13 | 0.094 | 0.047 | 0.057 | 0.033 | 0.032 | 0.050 | 0.056 |

$^a$Membrane area was 2 $cm^2$, solution volume was 2 ml.

The cleavage reaction of AMC from a free (unbound) peptide was tracked in parallel by fluorescence detection as a control for the cleavage reaction and fluorescence signal. The fluorescence values after 7 days incubation period were used to calculate the concentrations of the immobilized peptides on the surface of the membranes (Table 3).

TABLE 3

| Time of cleavage [h] | Overnight reaction | | | | | | 3 hours reaction | | Unbound peptide (control) |
|---|---|---|---|---|---|---|---|---|---|
| | PEG 4 mM | Jeff 4 mM | PEG 1 mM | Jeff 1 mM | PEG 0.2 mM | Jeff 0.2 mM | PEG 4 mM | Jeff 4 mM | |
| 4 | 0.214 | 0.171 | 0.080 | 0.049 | 0.063 | 0.076 | 0.087 | 0.082 | 8.709 |
| 22 | 0.302 | 0.262 | 0.113 | 0.093 | 0.029 | 0.032 | 0.103 | 0.117 | 14.410 |
| 28 | 0.350 | 0.275 | 0.103 | 0.109 | 0.061 | 0.063 | 0.115 | 0.148 | 14.765 |
| 47 | 0.356 | 0.332 | 0.167 | 0.138 | 0.062 | 0.068 | 0.134 | 0.144 | 15.501 |

TABLE 3-continued

| Time of cleavage [h] | Overnight reaction | | | | | | 3 hours reaction | | Unbound peptide (control) |
|---|---|---|---|---|---|---|---|---|---|
| | PEG 4 mM | Jeff 4 mM | PEG 1 mM | Jeff 1 mM | PEG 0.2 mM | Jeff 0.2 mM | PEG 4 mM | Jeff 4 mM | |
| 72 | 0.521 | 0.370 | 0.147 | 0.129 | 0.061 | 0.073 | 0.182 | 0.135 | 15.139 |
| 95 | 0.570 | 0.398 | 0.192 | 0.203 | 0.090 | 0.115 | 0.158 | 0.213 | 15.467 |
| 167 | 0.624 | 0.466 | 0.239 | 0.286 | 0.170 | 0.164 | 0.252 | 0.283 | 15.517 |

Measuring the Concentration of Free Amine Residues on the Membrane Surface:

Sorption/elution measurements of the dye Acid Orange 7 (orange II) were used to determine the concentration of free amino groups on a membrane. A solution of Acid Orange (0.0005M, pH=3) was added to the membranes. The membranes were then washed with triethanolamine 30%. The concentration of free amines was evaluated by absorption at 468 nm.

Inhibition of Biofilm Growth on Peptide Immobilized RO Membranes:

The membranes were tested the laboratory of Dr. Udi Banin, Bar-Ilan University a) Qualitative Measurements:

Biofilm was grown on different membranes in static conditions in which membranes were immersed in an *Enterobacter* culture. The cell content of the biofilm that developed on the membranes was exteriorated and evaluated using Bradford reagent for determining protein concentration.

b) Quantitative Measurements:

For biofilm growth measurements, modified membranes were tested in static conditions and in a flow-through system.

For static conditions membranes were glued with RTV 186 glue to a 1 cm×1 cm glass slides and were incubated in 24-wells plate, containing Green fluorescent protein (GFP) expressing *Pseudomonas aeruginosa* culture, for 18 hours (37° C.). Then, the membranes were washed with DDW to remove planktonic bacteria and the formed biofilm was detected by Leica DM 2500 confocal laser scanning microscope (CLSM, Wetzlar, Germany).

For the flow-through system, 1 cm×1 cm membranes were glued to a 2.6 cm×7.6 cm glass slide and the slide was placed in a flow cell. First, GFP expressing *Pseudomonas aeruginosa* was introduced to the cell and incubated for 1 hour. Then, the planktonic bacteria were washed out and sterile growth media was brought in to the cell with 50 ml/h flow rate. After 24 hours the sample was removed from the cell and biofilm fluorescence was detected by confocal laser scanning microscope. The dyed membranes were analyzed by a confocal laser scanning microscope.

Proteolytic Stability Assay of Peptides:

Stock solution (0.56 mg/ml) of each peptide was prepared by dissolving the peptide in PBS (pH=7.4). To each 90 µl of peptide solution 10 µl of enzyme solution, containing either a mixture of 0.5 µg trypsin (0.05 mg/ml) and 0.5 µg chymotrypsin (0.05 mg/ml) or 4 µg pronase E (0.4 mg/ml) in 0.001M HCl, was added. The enzymatic degradation of the peptide was monitored at controlled temperature of 25° C. by RP-HPLC with detection at 220 nm using Phenomenex C18 4.6×250 mm column with 5 µm particle size and 110 Å pore size. Elution gradient was: t=0 minutes, B=15%; t=5 minutes, B=15%; t=40 minutes, B=70%; t=42 minutes, B=95%; t=52 minutes, B=95% (flow rate 1 ml/minute).

Enzymes concentrations were determined by preliminary experiment that was performed to screen for concentrations allowing complete degradation of C-Modelin-1 within 1-2 hours. 10 µl of enzyme solution with varying concentrations were added to 90 µl of peptide solution (0.56 mg/ml) and enzymatic degradation of the peptide was monitored by RP-HPLC.

RO Membrane Performance Analysis:

The properties of RO membranes were evaluated before and after modification to estimate the effect of immobilization of AMPs on membrane performance. Properties that were measured are: Permeability (Lp), permeate flux, and salt rejection.

The membrane properties were measured in a cross-flow system equipped with two membrane cells. The system can generate a pressure up to 25 bar using nitrogen gas. The system has a container of ~1.8 L, and a pump that can generate flow up to 1350 mL/minute. The pressure inside the system can be controlled by a Nitrogen gas inlet and a pressure gauge; the temperature can be monitored with a water bath and a thermocouple thermometer. The parameters for all the analyses are temperature of 24° C., pressure of 15.2 bar, feed velocity of 1360 mL/minute, as indicated by the manufacturer in the membrane product sheet as the parameters for the membrane tests. The membrane area in these tests is 16.8 cm$^2$ (8.3 cm×2.2 cm).

Pure Water Permeability Analysis:

The pure water permeability analysis was carried out using LE-400 RO membranes that were compacted for 5-8 hours before the test with DDW water in the test's conditions. The measurements were done with DDW that were filled in the feed container, and after reaching a constant permeate flow. The permeate was collected 5-8 times for 5-12 minutes each time, and was weighted using analytical scale. The volume flux (Jv) was calculated, and by dividing it with the applied pressure the Lp value was obtained.

Salt Rejection Analysis:

The salt rejection measurements were done on the membranes after 5-8 hours of compacting with DDW. NaCl was used as the tested salt in the concentration of 2000 ppm.

The permeate was collected 7 times, for 10-12 minutes each time, and the conductivity was measured for each permeate collection. The feed was collected just before each measurement, to determine the feed conductivity since each measurement changed the salt concentration in the feed. The solution collections conductivities were measured by conductivity meter (WTW GmbH & Co., Weilheim, Germany).

General Synthetic Procedures

Peptide Synthesis Procedures:

The peptides were synthesized in the laboratory by the solid phase peptide synthesis (SPPS) method, using standard fluorenylmethoxy carbonyl (Fmoc) chemistry [E. Atherton, R. C. Sheppard, Solid Phase Peptide Synthesis, A Practical Approach, IRL Oxford University Press, New York, 1989]. The synthesis was carried out manually, using a glass reaction vessel for SPPS (Adams & Chittenden, Berkeley, Calif.) or automatically, using automated peptide synthesizer (CS336S automated peptide synthesizer, CS Bio Co, Menlo Park, Calif.).

The addition of a thiol group to a peptide, was done by adding a Cysteine amino acid (Cys, or C in the following schemes), to the N-terminus of the peptide.

Fmoc deprotection was achieved by treatment with 20% piperidine in DMF for 5 minutes and again for 25 minutes. After completion the resin was washed 4-5 times with DMF or NMP and 2 times with DCM, each wash lasted 0.5-2 minutes.

Amino Acid Coupling Procedure:

4-5 equivalents of protected amino acid and 4-5 eq of coupling reagent PyBOP or HBTU, respectively, were dissolved in DMF or DMF:DCM 1:1 solution. 8 eq of DIEA were added to the solution. After mixing it for 10 minutes the solution was added to the resin (previously swelled) and mixed for 2-3 hours for manual synthesis (using lab suspension mixer, MRC, Holon, Israel) or 1.5 hours for automated synthesis. After the reaction was completed the resin was washed 3 times with DMF and 2 times with DCM.

Amino Acid Coupling to Wang Resin:

The coupling performed using the symmetrical anhydride method. 10 eq of protected amino acid were dissolved in DCM (DMF was added if required). 5 eq of DIC were added to the solution and it was mixed for 20 minutes at 0° C. The DCM was evaporated using rotavapor, the remained mixture was dissolved in minimal amount of DMF and added to the resin. 0.1 eq of DMAP in DMF solution were added to the reaction vessel and it was mixed for 2-20 hours. After completion, the resin was washed 3 times with DMF and 2 times with DCM.

Final cleavage and removal of side-chain protecting groups: After the final Fmoc removal, the peptidyl-resin was dried and transferred to a polypropylene cartridge equipped with 20 μm hydrophobic polyethylene frit (Applied Separations, Allentown, Pa.). To cleave the peptide from Wang resin or Rink amide resin two scavenger cocktails were applied (6 ml solution for 0.1 mmol peptide): (1) 95% TFA, 2.5% tri-isopropylsilane (TIS), 2.5% DDW—for cleavage of standard peptide sequences. (2) 94% TFA, 1.5% TIS, 2.5% DDW, 2% 1,2-ethanedithiol- for cleavage of peptides with Cys(Trt) in their sequence. Standard cleavage time was 2 hours, with occasional mixing. If the sequence of the peptide consisted of two or more Arg(Pbf), cleavage time was longer in 2 hours for each additional Arg(Pbf) in the sequence. After completion, the solution was filtered into a 50 ml plastic tube and the resin was washed twice with 0.5 ml TFA. Solution volume was reduced to 2-4 ml using stream of nitrogen gas, then the peptide was precipitated by adding cold methyl tert-butyl ether (10 times the remained cocktail volume), centrifuged for 10 minutes at 2500 rpm (Labofuge 400 centrifuge, Thermo Fisher, Scientific, Waltham, Mass.) and the tert-butyl methyl ether was removed. The peptide was washed 2 more times with tert-butyl methyl ether (3 more, if 1,2-ethanedithiol was used in the cleavage cocktail). After drying under nitrogen gas, the peptide was dissolved in DDW or if necessary, acetic acid or acetonitrile (or both) were added, so that acetonitrile volume did not exceed 10% of the final volume. The dissolved peptide was then freeze-dried on a lyophilizer (Labconco FreeZone 2.5 Plus, Kans. City, Mo.) and analyzed by MALDI-TOF mass spectrometry and RP-HPLC.

Table 4 below lists peptides that were synthesized and used in the present invention and specifies their sequence, resin used for SPPS and scale of synthesis.

TABLE 4

| Peptide's Name[a] | Sequence[b,c] | Resin used | Scale of synthesis (mmol) |
|---|---|---|---|
| RWRW | RWRW-NH$_2$ | Rink resin | 0.2 |
| Hexapeptide4 | RRWWRF-NH$_2$ | Rink resin | 0.2 |
| CG$_3$-Hexapeptide-4 | CGGGRRWWRF-NH$_2$ | Rink resin | 0.2 |
| C-Modelin-1 | CKLWKKWAKKWLKLWKAW | Fmoc-Trp(Boc)-Wang resin | 0.2 |
| CG$_4$-Modelin-1 | CGGGGKLWKKWAKKWLKLWKAW | Fmoc-Trp(Boc)-Wang resin | 0.2 |
| CX-Modelin-1 | CXKLWKKWAKKWLKLWKAW | Fmoc-Trp(Boc)-Wang resin | 0.2 |
| C-Modelin-1-βAla | CKLWKKWAKKWLKLWKAW-βAla | Fmoc-β-Ala-Wang resin | 0.2 |
| All (D)-C-Modelin-1 | CKLWKKWAKKWLKLWKAW | Fmoc-D-Trp(Boc)-Wang resin | 0.1 |
| Pentapeptide-Amc | CIEPD-Amc | Fmoc-Asp(Wang resin)-Amc | 0.1 |

[a] CG3-Hexapeptide-4 and CG$_4$-Modelin-1 were synthesized by Karin Berliner during her M.Sc. thesis
[b] X = 6-aminohexanoic acid (Ahx), Amc = 7-amino-4-methylcoumarine
[c] Bold letters stand for D-amino acids Preparation of Armed Antimicrobial Peptides and Determination of Antimicrobial Activity Thereof Some antimicrobial peptides, as prepared according to the methods described above, were modified to include an arm molecule at their amino terminus, to test the effect of adding an arm on the antimicrobial activity. The arms included additional amino acids (CG3, G4, etc.), as well as 6-aminohexanoic acid (marked as X) and CX. The Synthetic data (MS, HPLC retention time and HPLC purities) of peptide-arm systems that were prepared are given in Table 5 below:

FIG. 1 shows the average biofilm formed by *Enterobacter* in the presence of C-Modelin-1-β-Ala, (All-D)-C-Modelin-1 and C— Modelin. $IC_{50}$ values were calculated from the graphs of FIG. 1 and are presented in Table 7.

TABLE 5

| Peptide's Name | Sequence[a] | Calculated MW [g/mol] | MS[b] [m/z] | Retention Time[c] [min] | Purity of Crude Peptide[c] | Purified Peptide[c] |
|---|---|---|---|---|---|---|
| CG$_3$-Hexapeptide4 | CGGGRRWWRF-NH$_2$ | 1279.5 | 1279.6 | 22.4 | 30%-50% | 95% |
| CX-Hexapeptide4 | CXRRWWRF-NH$_2$ | 1221.5 | 1221.9 | 23.2 | 27% | — |
| G$_4$-Modelin-1 | GGGGKLWKKWAKKWLKLWKAW | 2555.8 | 2555.6 | 28.2 | 20% | — |
| CG$_4$-Modelin-1 | CGGGGKLWKKWAKKWLKLWKAW | 2658.9 | 2658.4 | 28.4 | 15%-20% | 73% |
| CX-Modelin-1 | CXKLWKKWAKKWLKLWKAW | 2544.2 | 2543.4 | 29.0 | 15%-20% | 73% |
| CG$_4$-L$^6$P$^9$G$^{13}$F$^{16}$ | CGGGGYKLLKLLLPKLKGLLFKL-NH$_2$ | 2472.2 | 2471.6 | 31.1 | 27.6% | — |
| CX-Temporin-L | CXFVQWFSKFLGRIL-NH$_2$ | 1855.3 | 1856.1 | 35.9 | 22% | — |

[a]X - 6-aminohexanoic acid (Ahx), [b]MALDI-TOF MS, [c]Determined by RP-HPLC

The effect of linking the arm to a peptide, on the antimicrobial activity of the peptides was assessed by measuring the peptide activity in 96-microtitter plates in solution and comparing to activities of the normal peptides. Experiments were performed in water and in 3% NaCl solution. Table 6 presents the antimicrobial activity ($IC_{50}$) of peptide-arm systems, in water and in 3% NaCl solution. Values were extracted from dose-response curves.

TABLE 6

| Peptide[a] | $IC_{50}$ [μg/ml] Normal conditions | $IC_{50}$ [μg/ml] in 3% Aqueous NaCl |
|---|---|---|
| Hexapeptide-4 | 60 | 100 |
| CG$_3$-Hexapeptide-4 | 160 | 150 |
| CX-Hexapeptide-4 | 80 | >300 |
| Modelin-1 | 20 | 100 |
| G$_4$-Modelin-1 | 70 | 120 |
| CG$_4$-Modelin-1 | 100 | Not measured |
| CX-Modelin-1 | 60 | Not measured |
| L$^6$P$^9$G$^{13}$F$^{16}$ | 40 | 300 |
| CG$_4$-L$^6$P$^9$G$^{13}$F$^{16}$ | 110 | >300 |
| Temporin-L | 60 | 150 |
| CX-Temporin-L | >300 | Not measured |

[a]X-6-aminohexanoic acid (Ahx). Amino acid sequences appear in Table 5.

EXAMPLES

Example 1

Screening Peptides for Suitability in Preventing Biofilm Formation

Different concentration solutions of peptides, bought or prepared as detailed in the methods section above, were prepared by diluting a stock solution with 1% ACN. Stock solution was prepared by dissolving water soluble peptides in DDW:PBS1:1. PBS (pH=7.4) was prepared by adding to 800 ml DDW, 8 grams NaCl, 0.2 grams KCl, 1.44 grams Na$_2$HPO$_4$ and 0.2 grams KH$_2$PO$_4$.

TABLE 7

| Peptide | $IC_{50}$ [μg/ml] |
|---|---|
| C-Modelin-1 | 11 |
| C-Modelin-1-βAla | 4 |
| All-D C-Modelin-1 | 10 |

As demonstrated in FIG. 1 and in Table 7, the modified peptide (D)-C-Modelin-1 exhibited biofilm inhibition activity similar to the activity of the original, unmodified, C-Modelin-1 peptide. The $IC_{50}$ value of C-Modelin-1-βAla was lower than that of C-Modelin-1, indicating that insertion of the unnatural amino acid β-Ala to the sequence enhanced the antimicrobial activity of the peptide.

Peptide Stability:

The enzymatic degradation was monitored at a fixed temperature of 25° C. by RP-HPLC at 220 nm, as described before. Elution gradient started with 85% A/15% B for 5 minutes continued with 30% A/70% B for 35 minutes and ended with 5% A-95% B for 12 minutes.

All the enzymes were used in concentrations allowing complete degradation of C-Modelin-1 within 1-2.25 hours.

The digestion of the peptides C-Modelin-1 and C-Modelin-1-PAla by pronase E was first detected after 5 minutes and after 135 minutes the peptides were completely degraded. The L-peptides were even more susceptible to proteolytic degradation when treated with trypsin and chymotrypsin mixture and were completely digested after 70 minutes. All D C-Modelin-1, however, remained stable over 2 weeks when treated with the proteolytic enzymes. The results indicate a much higher stability (over 100-fold) of the (D)-C-Modelin-1 peptide compared with the unprotected Cys-Modelin-1.

Example 2

Linear Immobilization of Antimicrobial Peptides (AMPs) to Ro Membranes (3 Steps on-Membrane Method)

Linear immobilization of AMPS on RO membranes was done according to Scheme 2;

I. "Off membrane" modification of an antimicrobial peptide: A peptide such as Modelin-1 and Hexapeptide-4, was modified "off membrane" to add a thiol group to its N-terminus, as described in the general synthesis procedures above.

II. Addition of a Diamine Tether to the Membrane:

The RO membrane (FILMTEC LE-400, BW LE-30 and ESPA1 membranes, in three different experiments, were disinfected with 70% (v/v) ethanol and washed 3 times with DDW for 10 minutes, using sonication. Then, 1 equivalent (5-10 mM) of N-hydroxysulfosuccinimide sodium salt (sulfoNHS) and 1 eq(5-10 mM) of N-(3-dimethylaminopropyl)-N'-ethylcarbodiimide hydrochloride (EDC) were dissolved in sodium phosphate buffer solution (100 mM) at pH=6, added to the membranes (4 ml solution per 1 $cm^2$ membrane) and agitated for 1 hour. 5-10 mM of diamine poly(ethylene glycol) (diamine $PEG_{2000}$) or $Jeffamine_{500}$ were added to the solution and left on the shaker (Unimax 1010 orbital platform shaker, Heidolph, Kelheim, Germany) overnight. On the next day the membranes were washed with sodium phosphate buffer solution at pH=6, sodium phosphate buffer solution (100 mM) at pH=7.4 and DDW, 3 times each for 10 minutes, using sonication. After the wash, the membranes were kept in DDW.

In each case, the concentration of carboxyl groups was estimated using Toluidine blue dye. The yield of the modification was calculated according to carboxyl concentration of the unmodified membrane. The results for the LE-400 polyamide RO membrane are presented in Table 8.

TABLE 8

| Tether attached | COOH groups before modification$^a$ [mol/$cm^2$] | COOH groups after modification$^a$ [mol/$cm^2$] | Difference [mol/$cm^2$] | Calculated yield |
|---|---|---|---|---|
| Jeff amine | (2.07 ± 0.17) × $10^{-8}$ | (1.00 ± 0.10) × $10^{-8}$ | (1.07 ± 0.27) × $10^{-8}$ | 52% |
| PEG-AMINE | (2.07 ± 0.17) × $10^{-8}$ | (1.12 ± 0.12) × $10^{-8}$ | (0.95 ± 0.29) × $10^{-8}$ | 46% |

$^a$Area of the membranes = 12.0 $cm^2$, V = 12 ml

The results indicate that the attachment of the tether was successful, since the amount of the carboxyl groups on the surface of the membrane decreased after treating it with the spacer solution. The modification yields of both spacers were comparable.

Furthermore the properties of LE-400 membrane were evaluated before and after modification with Jeffamine-300, to estimate the effect of immobilization of AMPs on membrane performance. Properties that were measured are: Permeability (Lp), permeate flux, and salt rejection. The results are shown in Table 9 below.

TABLE 9

|  | Unmodified Membrane Cell 1 | Modified Membrane Cell 1 | Unmodified Membrane Cell 2 | Modified Membrane Cell 2 |
|---|---|---|---|---|
| LP (stdev) | 6.21 (0.21) | 4.44 (0.07) | 5.71 (0.66) | 4.55 (0.06) |
| Flux (Jv) | 97.35 (1.85) | 63.73 (2.43) | 92.96 (1.49) | 65.64 (2.34) |
| (stdev) $L/m^2$ * hr | | | | |
| Salt rejection (stdev) % | 96.41 (0.06) | 95.89 (0.07) | 95.68 (0.063) | 95.19 (0.09) |

From Table 9, it can be seen that although some decrease in the LP and in flux (~35%-27%) were observed after the modification took place, there was no change in the salt rejection.

A second comparative experiment was performed for for testing membrane properties after tether immobilization of $PEG_{3,000}$-diamine. there was about a ~700 decrease in the LP and in flux after the modification took place, and there was no change in the salt rejection.

III. Reaction of the Tethered-Membrane with a Maleimine Compound:

In the next step 6-maleimidohexanoic acid (MI) was attached to the tether arm (for example, the JeffAmine or PEG of the previous step), as follows: 1 eq (5-10 mM) of 6-maleimidohexanoic acid (MI-hexanoic acid), 1 eq (5-10 mM) of sulfoNHS and 1.05 eq (5-10 mM) of EDC were dissolved in sodium phosphate buffer solution pH=6 and agitated for 1 hour. Then the solution was added to the membranes (previously modified with diamine PEG2000 or Jeffamine-500; 4 ml per 1 cm2 membrane) and agitated overnight. On the next day the membranes were washed as described in step 11 and kept in DDW.

IV. Reaction of an MI-Terminated-Tethered-Membrane with the Thiol-Terminated AMP:

The thiol-terminated peptide, prepared in step 1, was dissolved in sodium phosphate buffer solution at pH=7.4, or in sodium phosphate buffer:DDW 1:1, so that the peptide concentration in solution was 3-7 mM. The solution was added to the modified membrane prepared in the previous step, which was covered and nitrogen gas was bubbled through the solution for 5 minutes to prevent oxidation of the thiol groups. After 2.5 hours on the shaker the membrane was washed as described in step 11.

Confirmation of Immobilization Reactions:

Both the FILMTEC LE-400 polyamide RO membrane and the ESPA1 polyamide RO membrane were dried and the water drop contact angle measurements of the membrane surface were taken, after each step of the immobilization process. The results are presented in Table 10.

TABLE 10

| RO membrane | Unmodified membrane | After Jeffamine modification | After PEGamine modification | After Jeffamine + MI modification | After Jeffamine + MI + C-Modelin-1 Modification |
|---|---|---|---|---|---|
| FILMTEC LE-400 | (77 ± 1)° | (68 ± 1)° | (74 ± 1)° | (66 ± 1)° | (75 ± 1)° |
| ESPA1 | (94 ± 2)° | (70 ± 2)° | (80 ± 2)° | (69 ± 1)° | (79 ± 2)° |

According to the results of the water drop contact angle, every step of the immobilization process (accept MI attachment) was followed by changes in the hydrophobicity of the membrane surface. It gives an indication that the immobilization process indeed took place.

Figure 2:
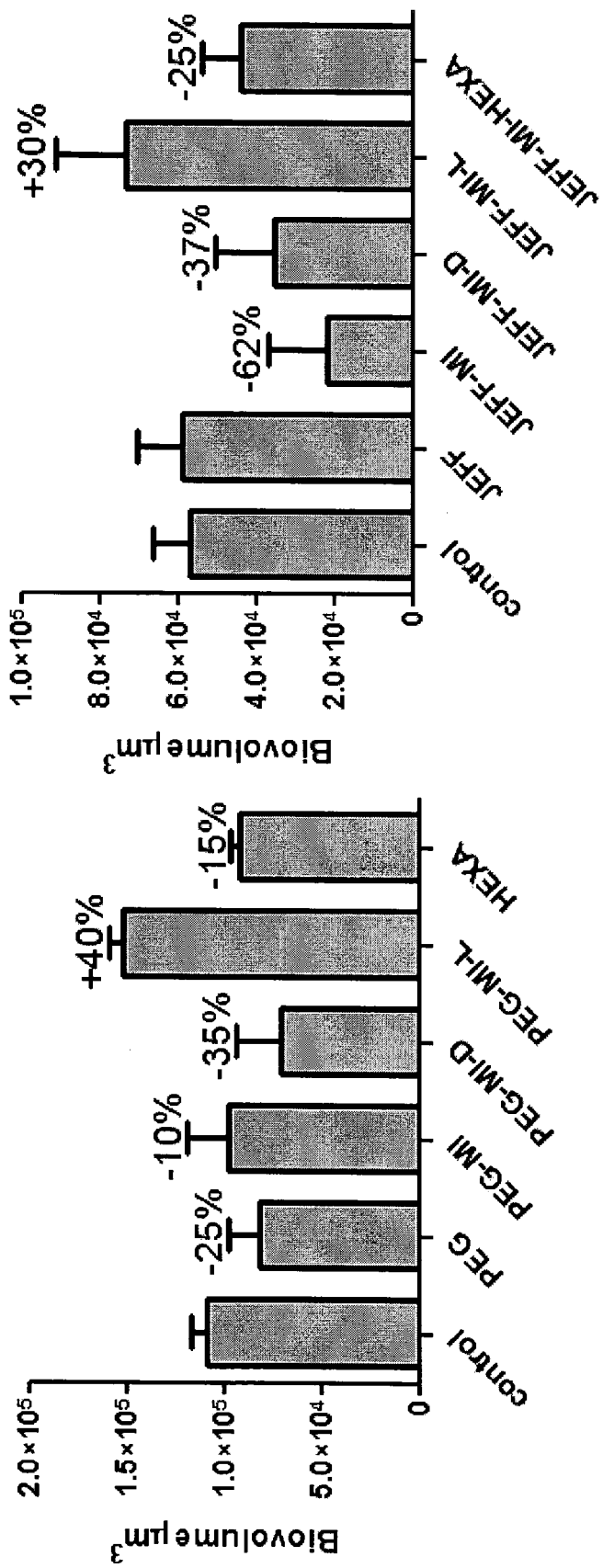
FIGS. 2, 3 represent the biovolume (cubic micrometers) versus different types of peptides.

The estimation of biofilm growth was also measured by using *P. Aeruginosa* in a flow cell; as can be seen in FIG. 2. This Figure shows the biofilm volume on membranes immobilized according to Scheme 3, using either PEG (left graph) and JeffAmine (right graph); on unmodified membranes (marked "control"), membrane modified with PEG diamine only (marked "PEG") or JeffAmine only (marked "JEFF"), with a PEG linked to maleimide-hexanoic acid (marked "PEG-MI"), with the final membrane attached to an all-D-Cys-Modelin-1 peptide via a PEG tether or Jeffamine tether and an MI linker (marked "PEG-MI-D" and "JEFF-MI-D", respectively), with the final membrane attached to a C-L-Modelin-1 peptide via a PEG tether or Jeffamine tether and an MI linker (marked "PEG-MI-L" and "JEFF-MI-L", respectively), and with the final membrane attached to a Hexapeptide-4 peptide via a PEG tether or Jeffamine tether and an MI linker (marked "HEXA and JEFF-MI-HEXA).

As can be seen in FIG. 2, the peptide Cys-All-D-Modelin-1 had the best inhibition among three peptides, when both PEG and JeffAmine tethers were used (35% and 37% inhibition, respectively). Membranes immobilized with peptide Hexapeptide-4 had 15% inhibition with PEG, and 25% inhibition with JeffAmine tether.

Example 3

Linear Immobilization of Antimicrobial Peptides (AMPs) to Ro Membranes (2 Steps on-Membrane Method)

Linear immobilization of AMPS on RO membranes was done according to Scheme 3.

I. "Off Membrane" preparation of a thiol-tethered-antimicrobial peptide:

A PEGylated All-D-Modelin-1 peptide (Cys-PEG-D-Modelin-1), and additional PEGylated peptides (as listed in Table 11 below) was prepared on SPPS, as described in the general preparation methods section above.

The PEGylation coupling step was performed by using Fmoc-NH-PEG$_{3000}$-CO—NHS or Trityl-S—C$_2$H$_4$—NH-PEG-COOSu (Rapp-polymere, Tubingen, Garmany). In the case of Fmoc-NH-PEG$_{3000}$-CO—NHS, coupling of Fmoc-Cys(Trityl)-OH was performed. The compounds were further characterized by MALDI-TOF mass spectrometry and analytical HPLC using C$_{18}$ column for polymers (300 Å voids).

Coupling of PEG to various Peptide-Resins (Table 11) was performed with solution of Fmoc-NH-PEG$_{3000}$-CO—NHS (1 eq.) and 1-Hydroxybenzotriazole (HOBt) (1 eq.) in DMF. After 3 hours, N,N'-Diisopropylcarbodiimide (DIC) (1 eq.) was added to the reaction vessel. The mixture was stirred for 24 hours and the solution was washed away. Then the same reaction was repeated. Then, coupling of Boc-Cys(Trt)-OH was done using 5 eq. The PEGylated peptide N-terminal Fmoc was deprotected with 20% piperidine in DMF. Final cleavage from the resin was achieved by a mixture of 95% trifluoroacetic acid (TFA), 2.5% triisopropylsilane and 2.5% water for 2 hours. After cleavage of the protecting groups, peptides were precipitated by addition of cold diethyl ether and dried with N$_2$ gas. The crude PEGylated peptide was dissolved in water, and dried in lyophilizer over night (−82° C., 0.01 mbar). Then, the crude PEG-peptides were purified by reversed-phase HPLC. The final products were more than 40% pure. Table 11 below specifies the sequences and purities of PEG-peptides that were prepared.

TABLE 11

| AMPs Name | Sequence | Calculated MW [g/mol] | MS$^a$ [m/z] | Retention Time [min] | Purity of Crude Peptide |
|---|---|---|---|---|---|
| L-Modelin-1 | KLWKKWAKKWLKLWKAW | 2327.9 | 2327.4 | 35.1 | 30%-45% |
| D-Modelin-1 | KLWKKWAKKWLKLWKAW | 2327.9 | — | 33.9 | 30%-45% |
| PEG-L-Modelin-1 | PEG-KLWKKWAKKWLKLWKAW | 5327.9 | +5300 | 28.4 | 15%-20% |
| Cys-PEG-L-Modelin-1 | PEG-KLWKKWAKKWLKLWKAW | 5431.1 | +5400 | 38.36 | 25%-30% |

$^a$MALDI-TOF MS

To evaluate whether attachment of a tether to the AMPs has an effect on the inhibitory potency, a PEGylated peptide (HS-PEG-D-Modelin-1) was prepared, and its inhibitory potency compared to that of the 'normal' peptide All-D-Modelin-1. Peptides were diluted in 2-fold serial dilutions, and the antibacterial activity of the peptides was determined in sterile 96-multititter plates. The $IC_{50}$ that was calculated from this experiment was 0.62 ug/ml, much lower than the D-Modelin-1. This means that the PEG tether slightly increased the antimicrobial effect of peptide D-Modelin-1.

To confirm the positive effect of a PEG tether, the assay was repeated by using D-Modelin-1 (crude) and HS-PEG-D-Modelin-1 that were prepared in the same synthesis. The results confirmed the finding of a slight increase in inhibition potency in the PEGylated peptide, as the calculated $IC_{50}$ from that experiment were 3 ug/ml for D-Modelin-1, and 0.4 ug/ml for the HS-PEG-D-Modelin-1.

II. Attachment of a Maleimide (MI) Linker to the RO Membrane:

The maleimide linker was linked to a reverse osmosis LE-400 membrane as described for attachment of diamine linkers in Example 2 (3-step procedure), by using 30 mM concentration of N-(2-Aminoethyl)-maleimide trifluoroacetate.

III. Attachment of the Thiol-Tethered-Antimicrobial Peptide to the MI-Terminated RO Membrane:

The HS-PEG-Modelin-1 was dissolved in sodium phosphate buffer pH=7.4: water 1:1 to a final concentration of 4.9 mM. The solution was added to the membrane (2 ml/1 cm2 membrane; previously modified with Maleimide linker), and the reaction was proceeded overnight; workup was performed as described for peptide attachment in Example 2 (3-steps procedure).

Confirmation of Immobilization Reactions:

Table 12 below shows the water drop contact angle measurements of membranes of each step, measured by placing 0.5 μl DDW on the membrane surface. For each membrane an average of five drops was calculated.

TABLE 12

| Sample Number: | Unmodified LE membrane | Maleimide-linker | Sample 3 MI-S-PEG-D-Modelin-1 |
|---|---|---|---|
| Average water contact angle$^a$: | 49.7° | 43.9° | 61.6° |
| Standard deviation | 2.5° | 3.3° | 9.0° |

The contact angle results are in agreement to other immobilizations that were performed, where the contact angle increases (hence more hydrophobic) upon immobilization of Modelin-1 (reasons were discussed above).

The loading of RO membranes with peptides was determined in two ways: in the first, by changes in the free carboxylic group concentration on the surface of the polyamide membrane, in the second by measuring enzymatic cleavage of 7-amino-4-methylcoumarine (AMC) residue.

Concentration of carboxyl groups on the surface of a membrane before and after attachment of spacers (linkers and/or tethers) was tested, as described above. The results of these tests are summarized in Table 13. Yield is calculated compared to the concentration of carboxyl group on an unmodified membrane.

TABLE 13

| Tether attached | COOH groups before modification [mol/cm$^2$] | COOH groups after modification [mol/cm$^2$] | Difference [mol/cm$^2$] | Calculated yield |
|---|---|---|---|---|
| Jeffamine 500 | $(2.07 \pm 0.17) \times 10^{-8}$ | $1.00 \pm (0.10) \times 10^{-8}$ | $1.07 \pm (0.27) \times 10^{-8}$ | 51.7% |
| PEG 2000 | $2.01 \pm 0.24) \times 10^{-8}($ | $1.50 \pm (0.14) \times 10^{-8}$ | $0.51 \pm (0.24) \times 10^{-8}$ | 25.4% |

As demonstrated in Table 13, the concentration of free carboxyl groups on the membrane surface is indeed reduced following attachment of a spacer or arm.

The results show that Jeffamine™ arms were attached at a concentration of $(1.07+0.27) \times 10^{-8}$ mol/cm$^2$ per membrane and that the PEG arms were attached at $(0.51+0.24) \times 10^{-8}$ mol/cm$^2$ per membrane. Thus, Jeffamine™ was attached twice as efficiently as PEG.

The concentration of free amine residues was calculated before and after attachment of Jeffamine™$_{500}$ and MI to the membrane. According to these calculations, the free amine concentration on the membrane surface increased after attachment of the arms and then decreased after modification with MI. The concentration of Jeffamine™ attached to the membrane is $5.55 \times 10^{-9}$ mol/cm$^2$. After attachment of MI, the free amines concentration decreased to a lower level than the concentration before modification. This indicates that the MI is attached to the free amines of the membrane and of the arm with calculated yield of 50%.

Water droplet angle of contact was tested before and after modification of the membranes with Jeffamine™$_{500}$ or PEG 2000 and MI, Jeffamine™ and MI and Jeffamine™, MI and the peptide C-Modelin-1. Two types of RO membranes were tested; BW and ESPA-1. The results of this test are summarized in Table 14.

TABLE 14

| RO membrane | Unmodified membrane | After Jeffamine modification | After PEG amine modification | After Jeffamine + MI modification | After Jeffamine + MI + C-Modelin-1 modification |
|---|---|---|---|---|---|
| BW | $(76.9 \pm 0.7)°$ | $(67.5 \pm 1.3)°$ | $(73.5 \pm 1.2)°$ | $(66.1 \pm 1.0)°$ | $(74.6 \pm 1.3)°$ |
| ESPA1 | $(94.0 \pm 1.7)°$ | $(69.8 \pm 2.2)°$ | $(79.7 \pm 1.9)°$ | $(68.8 \pm 1.1)°$ | $(78.7 \pm 1.5)°$ |

The results show that the membrane surface characteristics changed due to the different modifications of the membrane; after attachment of the hydrophilic arm (Jeffamine™ or PEG), the membrane surface became more hydrophilic. Attachment of MI lowered the angle of contact, and attachment of a peptide (which is more hydrophobic) raised the angle of contact.

Measuring Membrane Loading by AMC Cleavage:

The cleavage reaction of AMC from the unbound peptide terminated completely after 2 days, while the cleavage from the immobilized peptide continued over 7 days. The cleavage of AMC from the immobilized peptide required a longer period of time and the fluorescence values were lower because the access of the enzyme to the substrate was restricted.

The increase of fluorescence over time confirmed that the immobilization of the peptide indeed occurred. Moreover, changing the concentration of the peptide, the reaction time and the spacer, enabled to conclude that the MI group and peptide concentration in the reaction solution were the two prominent parameters that affected the concentration of the immobilized peptide.

The membranes that were modified with the highest peptide concentration (4 mM) and left over-night in the peptide solution, resulted with the highest amount of immobilized peptide per square centimeter of membrane area. When compared to the membranes that were modified with the same concentration of peptide solution but the reaction time was only 3 hours, the final concentration of the immobilized peptides was 1.7-2.6 timed lower and when compared to membranes that were left over night but modified with 1 mM and 0.2 mM of peptide solution, the final concentration of the immobilized peptides was 1.6-2.8 and 3-4 times lower, respectively.

Biological Activity of the Antimicrobial Membranes:

Quantitative and qualitative indications for biofilm formation on modified vs. non modified RO membranes were checked.

The results of the confocal microscope analysis of the biofilm that developed on the different membranes showing reduced biofilm formation on the modified membranes are summarized in Table 15.

TABLE 15

| Sample | Thickness (µm) | Biovolume (µm³) |
|---|---|---|
| Control membrane | 11.7 | $13.2 * 10^4$ |
| Linker-control | 34.7 | $23.7 * 10^4$ |
| C-$G_4$-Modelin-1 | 9.5 | $9.3 * 10^4$ |
| C-$G_3$-Hexapeptide-4 | 9.5 | $8.9 * 10^4$ |

Figure 3:
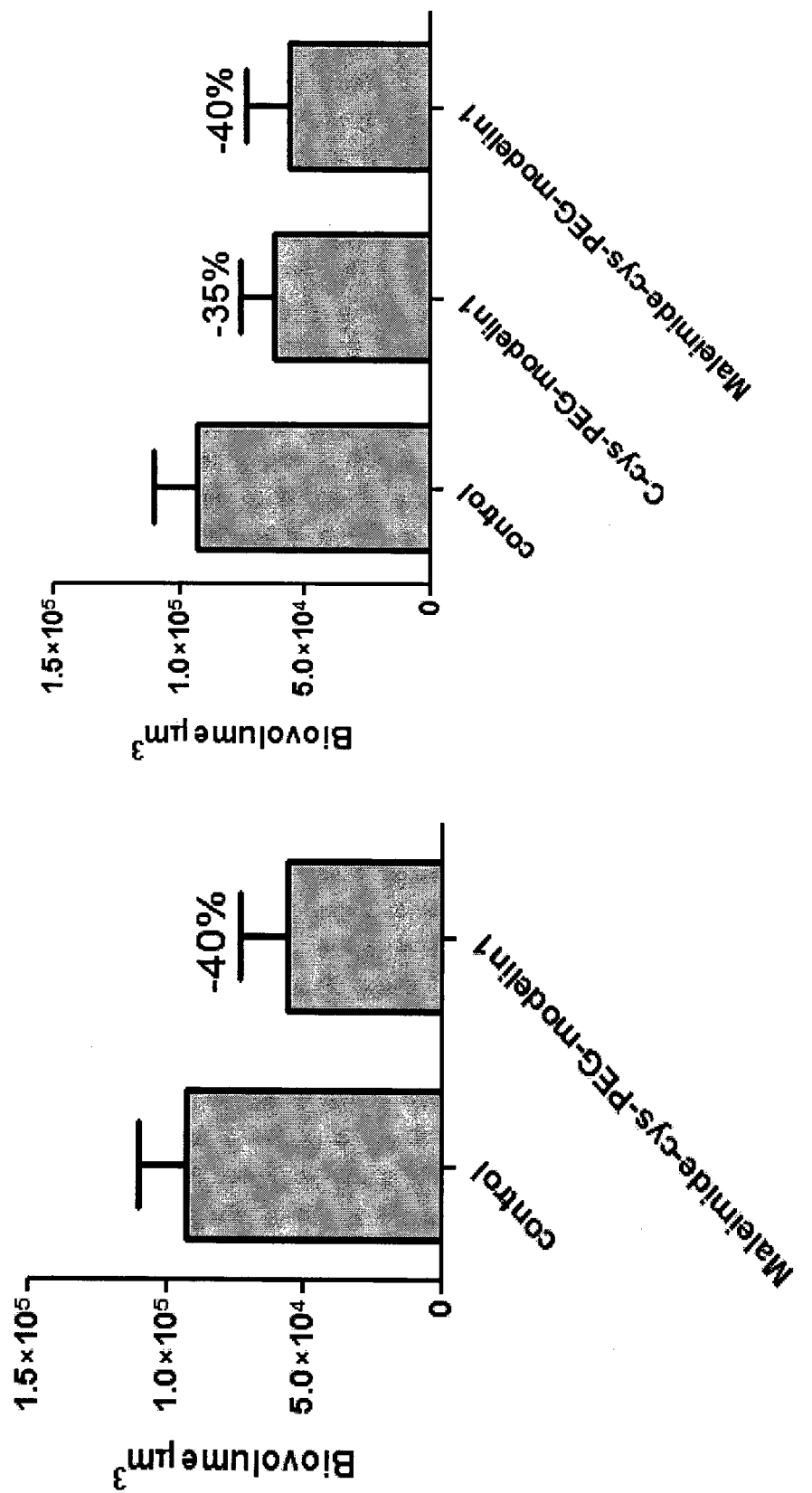

The inhibition of biofilm was also tested in a flow cell as described above. FIG. 3 presents the biofilm volume on RO membrane immobilized according to Scheme 3 (marked "Maleimide-cys-PEG-Modelin 1" and "C-cys-PEG-Modelin 1", regular linear immobilizaiton (3 steps method, as in Example 2)), in comparison to non-modified membrane (marked "control").

According to this figure, the biofilm on RO membrane immobilized with Cys-PEG-D-Modelin-1 was inhibited as compared to control membrane, with 35%-40% smaller biofilm volume in the peptide-immobilized membranes.

Example 4

Immobilization of Antimicrobial Peptides (AMPs) to RO Membranes by Graft Polymerization The immobilization of peptides on commercial brackish-water RO membrane type LE (FILMTEC, Dow Water Solutions) was done according to Schemes 7 and 8. Each step was characterized by measuring the water drop contact angle and by ATR-FTIR spectroscopy.

I. Graft Polymerization (Stage (1) in Scheme 8):

RO membranes were disinfected with 70% (v/v) ethanol and washed 3 times with DDW for 10 minutes, using sonication. Then two acrylic polymers MA: PEGM in 0.1:0.3 M or 0.2:0.2 M concentration respectively with 0.01 M initiators ($K_2S_2O_8$ and $K_2S_2O_5$) added to the membrane for 15 minutes. Subsequently the membranes washed 3×10 minutes in DDW using sonication. After the graft polymerization reaction, the soxhlet extractor was performed in order to clean the membrane and to confirm that the monomers did not adsorb to the surface of the membrane but have been attached covalently on the membrane surface. The soxhlet extractor was done in methanol for 3 hours. The membranes showed before and after soxhlet the same IR spectrum.

II. Attachment of 1,4-Butanediamine to the Membrane (Stage (2) in Scheme 8):

1 eq (5 mM) of N-hydroxysulfosuccinimide sodium salt (sulfoNHS), 1 eq (10 mM) of N-(3-dimethylaminopropyl)-N'-ethylcarbodiimide hydrochloride (EDC) and 3 eq (30 mM) of 1,4-butadiamine were dissolved in sodium phosphate buffer solution (100 mM) at pH=6. Afterwards, the solution was added to the membranes and was left on the shaker overnight. On the next day the membranes were washed with sodium phosphate buffer solution at pH=6; 3×10 minutes, sodium phosphate buffer solution (100 mM) at pH=7.4; 3×10 minutes, and 3×10 minutes in DDW, using sonication. After the wash, the membranes were kept in fresh DDW.

III. Attachment of Maleimide Linker (Stage (3) in Scheme 8):

1 eq (10 mM) of 6-maleimidohexanoic acid (MI-hexanoic acid), 1 eq (10 mM) of sulfoNHS and 1 eq (10 mM) of EDC were dissolved in sodium phosphate buffer solution pH=6 and agitated 30 minutes. Then the solution was added to the membranes (previously modified with diamine) and agitated overnight. On the next day the membranes were washed as described in section 2.2 and kept in fresh DDW.

IV. Immobilization of the Peptide (Stage (4) in Scheme 8):

A thiol-terminated peptide Cys-Modelin-1 was dissolved in sodium phosphate buffer pH=6: Isopropanol (1:1), so that peptide concentration in solution was 1 mM. Then, 400 µl ACN were added to 4 ml reaction vessel. The solution was added to the membrane (previously modified with diamine and MI-hexanoic acid), it was covered and nitrogen gas was bubbled through the solution for 5 minutes to prevent oxidation of the thiol side chain of Cys. The reaction was left on shaker or overnight. The membrane was washed 3×10 minutes in DDW using sonication.

The concentration of carboxyl groups on RO membrane surface before and after modification was estimated by staining with toluidine blue at basic pH, as detailed above. Table 16 shows concentration on the surface of FILMTEC LE-400 RO membrane before and after modification according to Scheme 7, using graft polymerization of methacrylic monomers of 0.1:0.3 M MA:PEGM, followed by attachment of 1,4-butadiamine in step 2. The yield of modification 2 (Scheme 7) was calculated based on decrease in carboxyl concentration, and is presented in Table 16.

TABLE 16

| Membrane modification | Carboxyl surface concentration by Toluidine blue | Calculated Yield/Ratio of Increase |
|---|---|---|
| a, Scheme 8 (unmodified) | $2.93 \times 10^{-8}$ mol/cm² | — |
| b, Scheme 8 | $2.15 \times 10^{-7}$ mol/cm² | 7-fold increase of carboxyl |
| c, Scheme 8 | $3.77 \times 10^{-8}$ mol/cm² | 82% yield |

The results indicate that the graft polymerization (step 1) was successful, increasing carboxyl groups by 7-fold, and the reaction with 1,4-butadiamine (step 2) had 82% yield.

Figures 4, 4A, 4B, 4C, 4D, 4E:
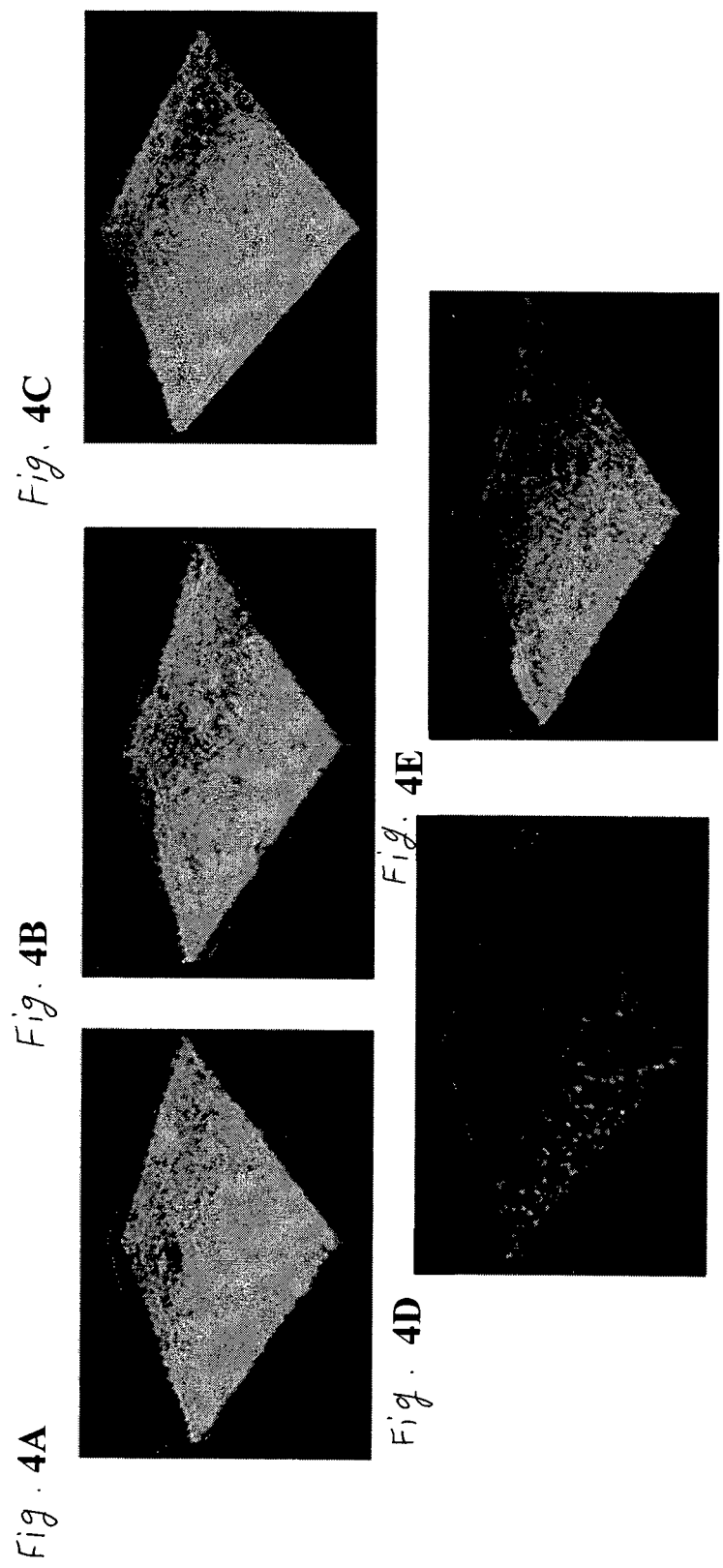
FIGS. 4-7 represent the biovolume of biofilm of RO membranes modified with Cys-Modelin-1.
Figure 5:
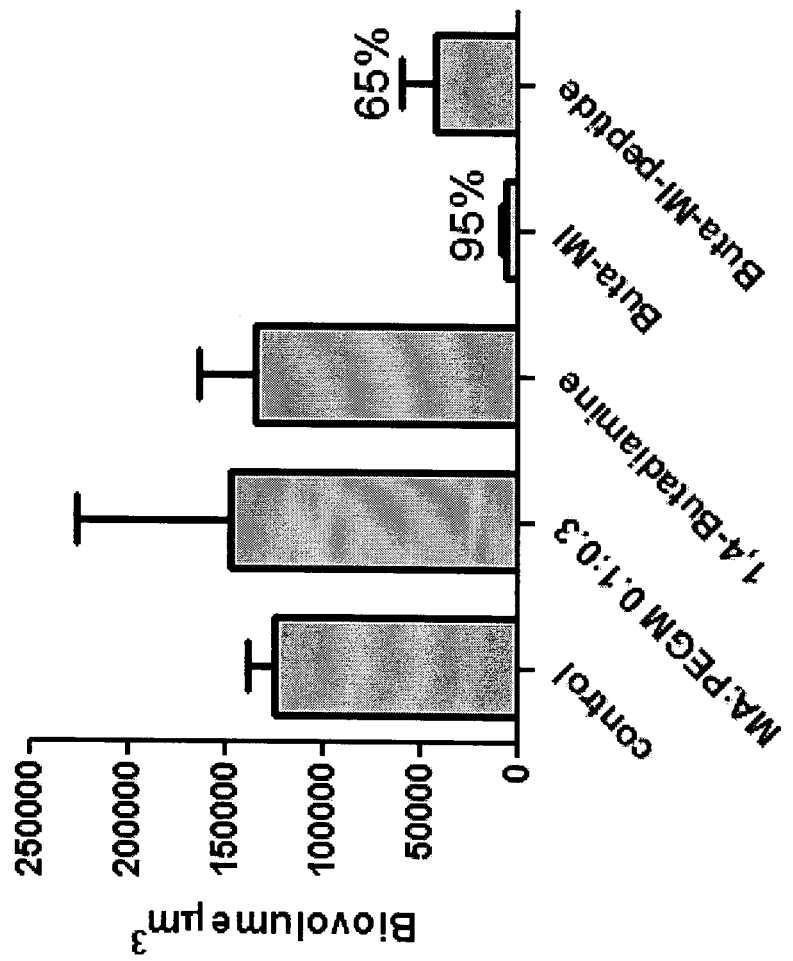

FIGS. 4 and 5 show the biovolume of biofilm on RO membranes modified with Cys-Modelin-1, whereas in FIG. 4: (A) is an unmodified membrane (control), (B) is after Graft polymerization (GP), (C) is after GP and 1,4-butadiamine, (D) is after GP, 1,4-butadiamine and MI (maleimide-hexanoic acid), and (E) is after GP, 1,4-butadiamine, MI and C-Modelin-1. FIG. 5 shows the volume of the biofilm formed on the examined membranes. As can be seen, immobilization with the peptide reduced biofilm growth by 65%; immobilization with maleimide group reduced biofilm growth by 95%.

Figure 6:
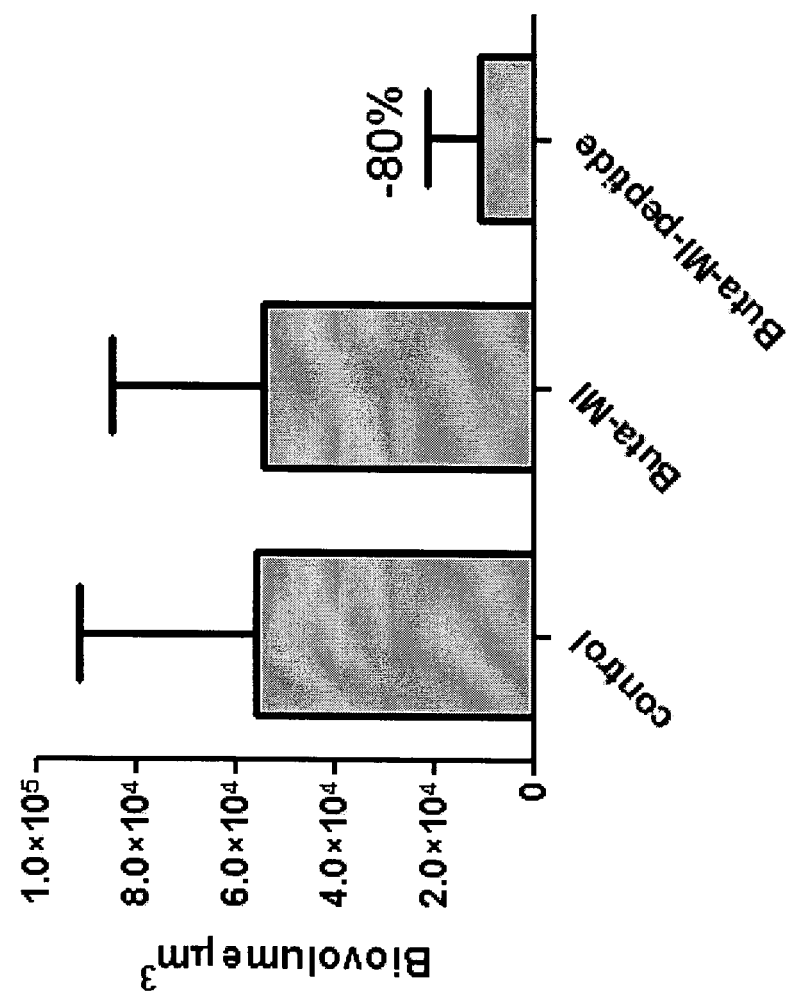

Another example for immobilization through multivalent system is shown in FIG. 6, showing the volume of the biofilm by graft polymerization with 0.2:0.2 M MA:PEGM and immobilization with All-D-Cys-Modelin-1. The results show good biofilm inhibition for peptide Cys-Modelin-1 (80%). The inhibition was very much dependent of the graft polymerization step: Grafting by 0.2:0.2 M of monomers PEG-MA:MA (see Scheme 6 for monomer structures) gave the best results.

Example 5

Immobilization of antimicrobial peptides (AMPs) to RO Membranes by a 3-step Graft Polymerization The immobilization of peptides on commercial brackish-water RO membrane type LE (FILMTEC, Dow Water Solutions) was done according to Scheme 9. Each step was characterized by measuring the water drop contact angle and by ATR-FTIR spectroscopy.

I. Graft Polymerization (Stage (1) in Scheme 9):

FILMTEC LE-400 RO membranes were graft polymerized as in Example 4, with the two acrylic polymers being PEGMA:MA in a 0.2:0.8M concentration respectively.

II. Addition of an Amine Alkyl Linker (Stage (2) in Scheme 9):

To the graft-polymerized membrane an aminoethyl-maleimide linker was coupled as described for attachment of diamine linkers in Example 2 (3-step procedure), except that 30 mM concentration of the N-(2-Aminoethyl)-maleimide trifluoroacetate was used, instead of 5-10 mM. The rest of the procedure was the same.

III. Immobilization of a Tethered Peptide (Stage (3) in Scheme 9):

Off-membrane HS-PEG3000-all-D-Modelin-1 or Cys-PEG3000-all-D-Modelin-1 (PEGylated-thiol AMP) was prepared (see example 3, stage I).

Coupling of HS-PEG3000-all-D-Modelin-1 or Cys-PEG3000-all-D-Modelin-1 to the membrane: The tethered AMP was dissolved in sodium phosphate buffer solution at pH=7.4, or in sodium phosphate buffer:DDW 1:1, so that the peptide concentration in solution was 3-7 mM. The solution was added to the modified membrane prepared in the previous step, which was covered and nitrogen gas was bubbled through the solution for 5 minutes to prevent oxidation of the thiol groups. The reaction proceeded on a shaker overnight, then the membrane workup was performed as described for peptide attachment in Example 2 (3-steps procedure).

Figure 7:
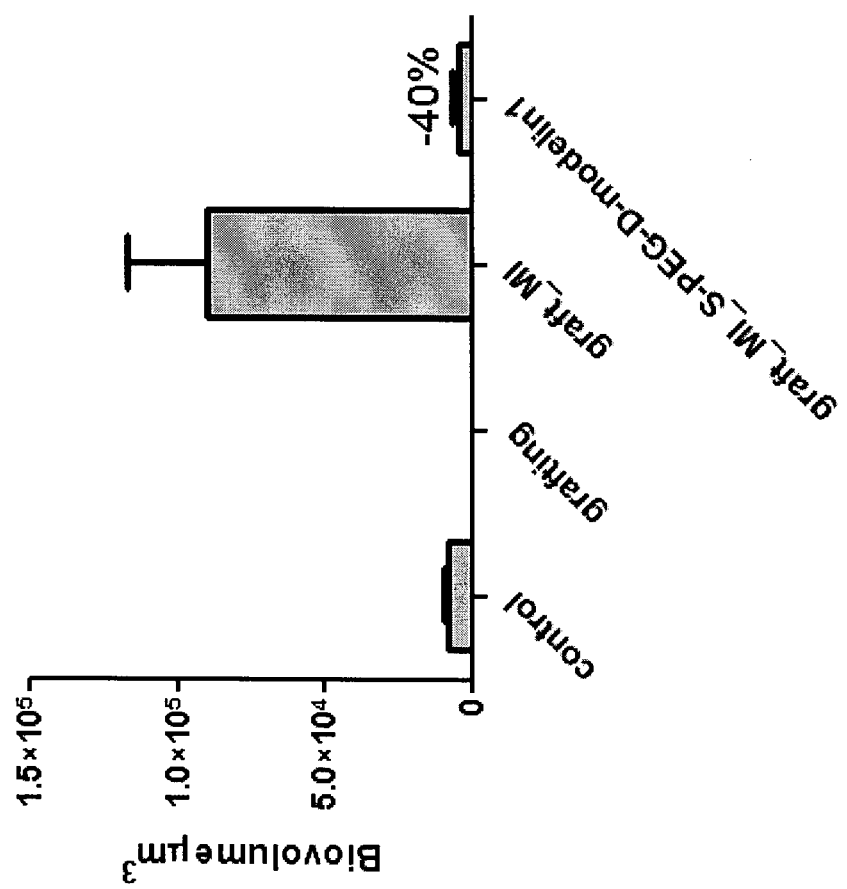

FIG. 7 shows the biovolume according to an *Enterobacter* assay of the various stages of prepared membrane: After stage (1) of the graft polymerization (grafting), after the attachment of MI linker of aminoethyl-maleimide (graft_MI), and after the attachment of HS-PEG3000-D-Modelin-1 (graftMIS-PEG-D-Modelin1). The final immobilized peptide reduced biofilm formation by 40% relative to control membrane.

Example 6

Immobilization of AMPS Through Multivalent System by Use of Dendrimers

The immobilization of peptides on commercial RO membrane type was done according to Scheme 10.

I. Attachment of N-(2 Aminoethyl)-maleimide Trifluoroacetate Salt to the Membrane by Amide Bond:

A maleimide linker was linked as described for attachment of diamine linkers in 3-step procedure (Example 2), by using 30 mM concentration.

II. Attachment of HS-PEG-Peptide to RO Membranes Through Maleimide Linker:

The HS-PEG-Modelin-1 was dissolved in sodium phosphate buffer pH=7.4: water 1:1 to a final concentration of 4.9 mM. The solution was added to the membrane (previously modified with Maleimide linker), and reaction was proceeded overnight; workup as described for peptide attachment in 3-steps procedure.

The invention claimed is:

1. An antimicrobial water treatment membrane comprising a water treatment membrane, covalently attached to one or more antimicrobial peptides or derivatives of said one or more antimicrobial peptides via one or more tether molecules, wherein said tether:
   a) is an oligomer or a polymer having a molecular weight of at least 300 grams/mol,
   b) has an extended length, in an aqueous environment, of at least 1.5 nanometers; and
   c) has a ratio between said molecular weight and said extended length which is lower than 1,200 g/mol per 1 nanometer;
   and further wherein said antimicrobial peptide:
   d) has an $IC_{50}$ value of up to 200 µg/ml and higher than 0, against at least one biofilm-forming microorganism, and
   e) is stable against proteolysis for at least 1 week.

2. The antimicrobial water treatment membrane of claim 1, wherein said antimicrobial peptide and/or said membrane is attached to said tether via a bond selected from the group consisting of an amide bond, a thioether bond, a carbon-carbon bond, a carbon-nitrogen bond, an azide-alkyne bond, a hydrazine-aldehyde bond, an Avidin-biotin complexation and combinations thereof.

3. The antimicrobial water treatment membrane of claim 1, wherein said water treatment membrane is a reverse osmosis membrane, a nanofiltration membrane or an ultrafiltration membrane.

4. The antimicrobial water treatment membrane of claim 3, wherein said water treatment membrane is a thin film composite membrane.

5. The antimicrobial water treatment membrane of claim 1, wherein said antimicrobial peptide is an all-(D)-amino acid analog of a natural peptide, or an N-methylated analog of a natural peptide.

6. The antimicrobial water treatment membrane of claim 1, wherein said antimicrobial peptide is linked to said tether via an N-terminal side of said antimicrobial peptide.

7. The antimicrobial water treatment membrane of claim 1, wherein said peptide is antimicrobially active in an *Enterobacter* 96-well assay.

8. The antimicrobial water treatment membrane of claim 7, wherein said peptide is antimicrobially active in a 3% aqueous salt solution.

9. The antimicrobial water treatment membrane of claim 8, wherein said peptide is a modified Modelin-1 peptide or a modified Hexpeptide-4.

10. The antimicrobial water treatment membrane of claim 1, wherein said tether molecule is selected from the group consisting of: a Poly Ethylene Glycol (PEG) polymer, water soluble polyethers that that are derivatives of polyethylene-glycol, a poly-acrylamide polymer, a poly-(D)-lysine polymer, a polyacrylate, a diamine polymer, poly-(D)-Aspartic acid and combinations thereof.

11. The antimicrobial water treatment membrane of claim 1, wherein said tether molecule is a multivalent molecule.

12. The antimicrobial water treatment membrane of claim 1, having a structure selected from structures I-IV:

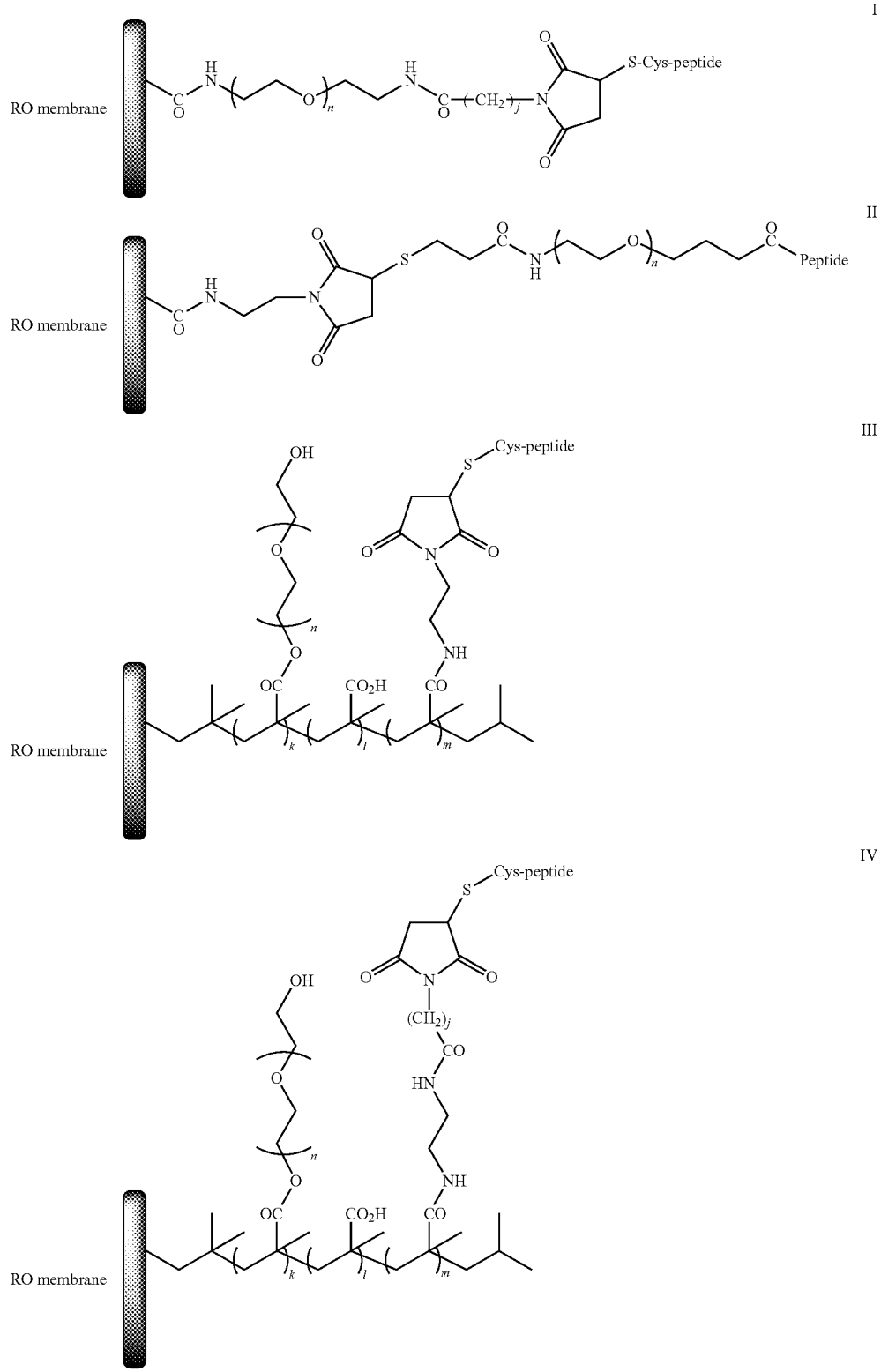

Wherein j, k, l, m and n are integers independently larger than 1, and the peptide is selected from the group consisting of hexapeptide-4, Modelin-1, All-D-Modelin-1 and combinations thereof.

13. A process for preparing an antimicrobial water treatment membrane, said process comprising covalently attaching one or more antimicrobial peptides or derivatives of said one or more antimicrobial peptides to a water treatment membrane, via a tether molecule, wherein said tether;
  a) is an oligomer or a polymer having a molecular weight of at least 300 grams/mol,
  b) has an extended length, in an aqueous environment, of at least 1.5 nanometers; and
  c) has a ratio between said molecular weight and said extended length which is lower than 1,200 g/mol per 1 nanometers;
  and further wherein said antimicrobial peptide;
  d) has an $IC_{50}$ value of up to 200 μg/ml and higher than 0, against at least one biofilm-forming microorganism, and
  e) is stable against proteolysis for at least 1 week.

14. The process of claim 13, wherein said tether has at least two terminating groups, each being independently selected from a maleimide (MI) group, 6-aminohexanoic acid, a thiol group, an azide group, an amine group, a carboxyl group or an acetylene group.

15. The process of claim 13, wherein said membrane and said peptide independently have at least one terminating group being selected from a maleimide group, 6-aminohexanoic acid, a thiol group, an azide group, an amine group, a carboxyl group or an acetylene group.

16. The process of claim 13, wherein part of said process is conducted "off membrane".

17. An antimicrobial water purification process, comprising contacting a water source selected from the group consisting of sea-water, waste water, brackish water, industrial water, irrigation water, drinking water and combinations thereof, with an antimicrobial water treatment membrane comprising a water treatment membrane, covalently attached to one or more antimicrobial peptides or derivatives of said one or more antimicrobial peptides via one or more tether molecules, wherein said tether:
  a) is an oligomer or a polymer having a molecular weight of at least 300 grams/mol,
  b) has an extended length, in an aqueous environment, of at least 1.5 nanometers; and
  c) has a ratio between said molecular weight and said extended length which is lower than 1,200 g/mol per 1 nanometer;
  and further wherein said antimicrobial peptide:
  d) has an $IC_{50}$ value of up to 200 μg/ml and higher than 0, against at least one biofilm-forming microorganism, and
  e) is stable against proteolysis for at least 1 week.

* * * * *